US006960588B1

(12) United States Patent
Martin

(10) Patent No.: US 6,960,588 B1
(45) Date of Patent: Nov. 1, 2005

(54) TRYPTASE INHIBITORS

(75) Inventor: Thomas Martin, Constance (DE)

(73) Assignee: Altana Pharma AG, Contance (DE)

( * ) Notice: Subject to any disclaimer, the term of this patent is extended or adjusted under 35 U.S.C. 154(b) by 190 days.

(21) Appl. No.: 10/070,279

(22) PCT Filed: Sep. 12, 2000

(86) PCT No.: PCT/EP00/08899

§ 371 (c)(1),
(2), (4) Date: Mar. 6, 2002

(87) PCT Pub. No.: WO01/19809

PCT Pub. Date: Mar. 22, 2001

(30) Foreign Application Priority Data

Sep. 14, 1999 (EP) ................................. 99118233

(51) Int. Cl.$^7$ ..................... A61K 31/497; A61K 31/24; A01N 37/12; A01N 37/44; C07C 233/00

(52) U.S. Cl. ................. 514/252.11; 514/540; 514/595; 514/619; 514/621; 514/636; 514/654; 544/386; 544/400; 544/403; 560/25; 560/34; 560/35; 560/41; 560/158; 560/163; 560/168; 564/156

(58) Field of Search ............................. 560/25, 34, 35, 560/41, 158, 163, 168; 564/156; 544/386, 544/400, 403; 514/252.11, 540, 595, 619, 514/621, 636, 654

(56) References Cited

FOREIGN PATENT DOCUMENTS

| | | |
|---|---|---|
| WO | 95/32945 | 12/1995 |
| WO | 96/09297 | 3/1996 |
| WO | 98/04537 | 2/1998 |
| WO | 99/12918 | 3/1999 |
| WO | 99/24395 | 5/1999 |
| WO | 99/24407 | 5/1999 |
| WO | 99/40083 | 8/1999 |

OTHER PUBLICATIONS

Hawley's Condensed Chemical Dictionary, Twelfth ed., p. 594, Van Nostrand Reinhold © 1993.*
McGraw-Hill Dictionary of Chemical Terms, p. 200, McGraw-Hill, Inc. © 1985.*
Concise Encyclopedia Chemistry, p. 490, Walter de Gruyter & Co. © 1993.*
Rodbotten et al, "Stereoselective Synthesis of Alkynylglycines and a,a'-Alkynyl-Bridged Bis(glycines)" Acta Chemica Scandinavica, vol. 51, pp. 873-880, (1997).*
Crisp et al, "Elaboration of the Side-Chain of Amino Acid Derivatives by Palladium Catalysed Couplings" Tetrahedron, vol. 53(51), pp. 17489-17500 (1997).*
Burgess, "Mast Cell Tryptase as a Target for Drug Design" Drug News Perspectives, vol. 13(3), pp. 147-157 (Apr. 2000).*
Wright et al, "Inhibition of Allergen-Induced Pulmonary Responses by the Selective Tryptase Inhibitor 1,5-bis-{4-[(3-Carbamidoyl-benzenesulfonylamino)-methyl]-phenoxy}-pentane (AMG-126737)" Biochemical Pharmacology, vol. 58, pp. 1989-1996 (1999).*
West, Anthony R. "Solid State Chemistry and its Applications" Wiley, New York, pp. 358 and 365 (1988).*
Rice, K.D., et al., "Inhibitors of Tryptase for the Treatment of Mast Cell-Mediated Diseases", *Current Pharmaceutical Design*, V. 4, No. 5, pp. 381-396, (1998).
Krishna, et al., "Inhibition of mast cell tryptase by inhaled APC 366 attenuates allergen-induced late-phase airway obstruction in asthma", *J. Allergy Clin. Immunol.*, Jun., 2001, pp. 1039-1045.
Rice, et al., "Dibasic Inhibitors of human mast cell tryptase. Part 2: Structure-Activity Relationships and Requirements for Potent Activity", Bioorganic & Medicinal Chemistry Letters 10, pp. 2361-2366 (2000).

* cited by examiner

*Primary Examiner*—Richard L. Raymond
*Assistant Examiner*—Zachary C. Tucker
(74) *Attorney, Agent, or Firm*—Nath & Associates PLLC; Joshua B. Goldberg; Sheldon M. McGee

(57) ABSTRACT

Compounds of formula (I)

(I)

```
 B1-A1-B3-A3-B5-A5-K1
/
M
\
 B2-A2-B4-A4-B6-A6-K2
```

in which M, B1, B2, B3, B4, B5, B6, A1, A2, A3, A4, A5, A6, K1 and K2 have the meanings as indicated in the description, are novel effective tryptase inhibitors.

12 Claims, No Drawings

TRYPTASE INHIBITORS

FIELD OF APPLICATION OF THE INVENTION

The invention relates to novel tryptase inhibitors which are used in the pharmaceutical industry for preparing medicaments.

KNOWN TECHNICAL BACKGROUND

The international applications WO95/32945, WO96/09297, WO98/04537, WO99/40073, WO99/40083, WO99/12918, WO99/24395 and WO99/24407 describe low-molecular-weight compounds for use as tryptase inhibitors.

DESCRIPTION OF THE INVENTION

It has now been found that the compounds of the formula I, which are described in more detail below, have surprising and particularly advantageous properties.

The invention provides compounds of the formula I

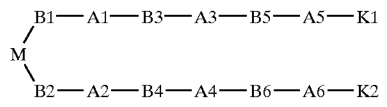

(I)

in which

A1 and A2 are identical or different and are —C(O)—, —NH—, —O— (oxygen), —S—(sulfur), $—S(O)_2—$, $—S(O)_2—NH—$, $—NH—S(O)_2—$, —C(O)—NH—, —NH—C(O)—, —O—C(O)—, —C(O)—O— or a bond, A3 and A4 are identical or different and are —C(O)—, —O—, —S—, —NH—, —O—C(O)—, —C(O)—O—, —C(O)—NH—, —NH—C(O)— or a bond, or are selected from the group consisting of

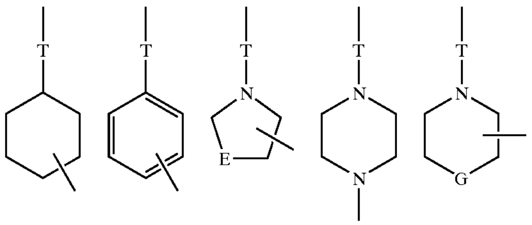

where

E is —O— (oxygen), —S—(sulfur) or $—CH_2—$ (methylene),

G is —O— (oxygen) or $—CH_2—$ (methylene), and

T is the group —C(O)— or a bond,

A5 and A6 are identical or different and are —C(O)—, —NH—, —O—, —S—, —C(O)—NH—, —NH—C(O)—, —O—C(O)—, —C(O)—O—, —NH—C(O)—NH— or a bond, M is a central building block selected from the group below

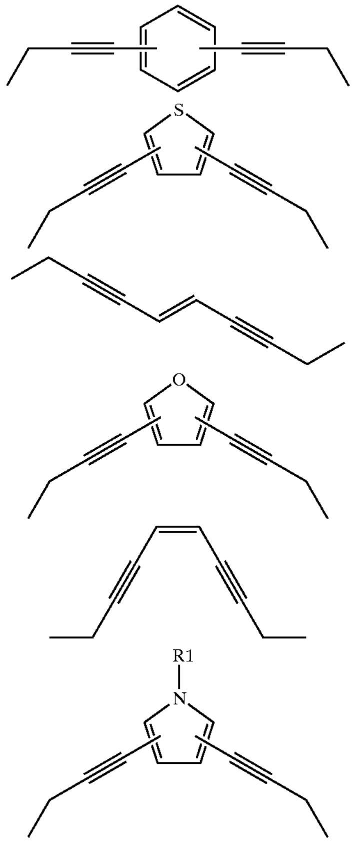

where

R1 is hydrogen, 1–4C-alkyl or 1–4C-alkylcarbonyl,

K1 is $—B7—(C(O))_m—B9—X1$, $—B7—(C(O))_m—B9—Y1$ or $—B7—(C(O))_m—B9—Z1—B11—X1$,

K2 is $—B8—(C(O))_p—B10—X2$, $—B8—(C(O))_p—B10—Y2$ or $—B8—(C(O))_p—B10—Z2—B12—X2$,

B1, B2, B3, B4, B5 and B6 are identical or different and are a bond or 1–4C-alkylene, B7, B8, B9, B10, B11 and B12 are identical or different and are a bond or 1–4C-alkylene, m is 0 or 1, p is 0 or 1, X1 and X2 are identical or different and are selected from the group consisting of

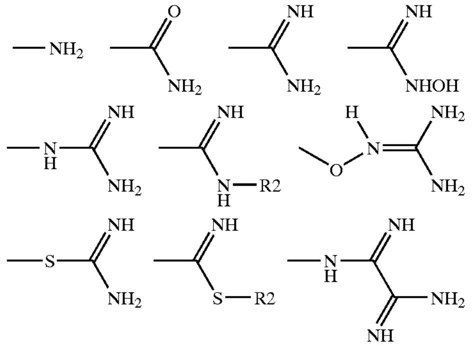

-continued

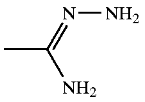

where

R2 is 1–4C-alkyl,

Y1 and Y2 are identical or different and are a 4–11C-heteroaryl or 2–7C-heterocycloalkyl radical containing at least one ring nitrogen, Z1 and Z2 are identical or different and are 5–12C-arylene, 5–12C-heteroarylene, 3–8C-cycloalkylene or 3–8C-heterocycloalkylene, where each arylene, heteroarylene, cycloalkylene, heterocycloalkylene, heteroaryl or heterocycloalkyl may additionally for its part be substituted by one, two or three substituents selected from the group consisting of hydroxyl, halogen, nitro, cyano, amino, 1–4C-alkyl, 1–4C-alkoxy, 1–4C-alkoxycarbonyl, 1–4C-alkylcarbonyloxy, carboxyl or aminocarbonyl, and where on the direct route between the terminal nitrogen atoms 20 to 40, preferably 25 to 40, bonds have to be present, the salts of these compounds, and the N-oxides of the nitrogen-containing heteroaryls, heterocycloalkyls, heteroarylenes and heterocycloalkylenes, and their salts, where all those compounds are excluded in which one or more of the variables B1, B2, B3, B4, B5, B6, B7, B8, B9, B10, B11 or B12 may assume the meaning of a bond resulting in the direct linkage of two heteroatoms or two carbonyl groups.

1–4C-Alkyl represents straight-chain or branched alkyl radicals having 1 to 4 carbon atoms. Examples which may be mentioned are the butyl, isobutyl, sec-butyl, tert-butyl, propyl, isopropyl, ethyl and the methyl radicals.

1–4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and preferably the ethoxy and methoxy radicals.

1–4C-Alkoxycarbonyl represents a carbonyl group to which is attached one of the abovementioned 1–4C-alkoxy radicals. Examples which may be mentioned are the methoxycarbonyl [$CH_3O—C(O)—$] and the ethoxycarbonyl [$CH_3CH_2O—C(O)—$] radicals.

1–4C-Alkylcarbonyl represents a radical which, in addition to the carbonyl group, contains one of the abovementioned 1–4C-alkyl radicals. An example which may be mentioned is the acetyl radical.

1–4C-Alkylcarbonyloxy represents a carbonyloxy group to which is attached one of the abovementioned 1–4C-alkyl radicals. An example which may be mentioned is the acetoxy [$CH_3C(O)—O—$] radical.

For the purpose of the invention, halogen is bromine, chlorine and fluorine.

1–4C-Alkylene represents straight-chain or branched 1–4C-alkylene radicals, for example the methylene ($—CH_2—$), ethylene ($—CH_2—CH_2—$), trimethylene ($—CH_2—CH_2—CH_2—$), tetramethylene ($—CH_2—CH_2 CH_2—CH_2—$), 1,2-dimethylethylene [$—CH(CH_3)—CH(CH_3)—$], 1,1-dimethylethylene [$—C(CH_3)_2—CH_2—$], 2,2-dimethylethylene [$—CH_2—C(CH_3)_2—$], isopropylidene [$—C(CH_3)_2—$] or the 1-methylethylene [$—CH(CH_3)—CH_2—$] radicals.

If m is 0, the group $—(C(O))_m—$ is a bond.

If p is 0, the group $—(C(O))_p—$ is a bond.

4–11C-Heteroaryl represents a—if desired substituted—mono- or bicyclic aromatic hydrocarbon which contains 4 to 11 C atoms and at least one ring nitrogen atom; in addition, one or more of the carbon atoms may be replaced by ring heteroatoms selected from the group consisting of O, N and S. In the case of bicycles, at least one of the rings is aromatic. Examples which may be mentioned are pyrid-4-yl, pyrid-3-yl, pyrimidin-5-yl, imidazol-1-yl and benzimidazol-5-yl.

2–7C-Heterocycloalkyl represents a—if desired substituted—monocyclic saturated or partially saturated hydrocarbon which contains 2 to 7 C atoms and at least one ring nitrogen atom; in addition, one or more carbon atoms may be replaced by ring heteroatoms selected from the group consisting of O, N and S. Examples which may be mentioned are piperid-4-yl, piperazin-1-yl, pyrrolidin-2-yl, pyrrolidin-3-yl, imidazolidin-1-yl, imidazolidin-2-yl, imidazolidin-4-yl and morpholin-2-yl.

5–12C-Arylene represents a—if desired substituted—divalent mono- or bicyclic aromatic hydrocarbon radical having 5 to 12 C atoms, where in the case of bicyclic aromatic hydrocarbon radicals at least one of the rings is aromatic. The free valencies can both be located at the aromatic, both at the nonaromatic or one at the aromatic and one at the nonaromatic ring. Examples which may be mentioned are 1,4-phenylene, 1,3-phenylene, 1,4-naphthylene and 2,6-naphthylene.

5–12C-Heteroarylene represents an arylene radical as defined above in which 1 to 4 C atoms are replaced by heteroatoms selected from the group consisting of O, N and S. Examples which may be mentioned are 2,5-furylene, 2,5-pyrrolylene, 4,2-pyridylene, 5,2-pyridylene, 2,5-indolylene, 2,6-indolylene, 3,5-indolylene, 3,6-indolylene, 3,5-indazolylene, 3,6-indazolylene, 2,5-benzofuranylene, 2,6-quinolinylene and 4,2-thiazolylene.

3–8C-Cycloalkylene represents a—if desired substituted—divalent monocyclic saturated or partially saturated hydrocarbon radical having 3 to 8 C atoms. Examples which may be mentioned are the 1,3-cyclopentylene, the 1,3-cyclohexylene and preferably the 1,4-cyclohexylene radicals.

3–8C-Heterocycloalkylene represents a cycloalkylene radical as defined above in which 1 to 3 C atoms are replaced by heteroatoms selected from the group consisting of O, N and S. Examples which may be mentioned are the 1,4-piperidinylene, 1,4-piperazinylene, 2,5-pyrrolidinylene, 4,2-imidazolidinylene and preferably the 4,1-piperidinylene radicals.

Preferred meanings of the groups X1 and X2 are amino, aminocarbonyl, amidino and guanidino.

The particularly preferred meaning of the groups X1 and X2 is amino.

By definition, the groups Z1 and Z2 are located between the groups B9 and B11 (—B9—Z1—B11—) and B10 and B12 (—B10—Z2—B12—), respectively. Accordingly, in the divalent groupings mentioned by way of example (for example 2,6-indolylene), the first number indicates the point of attachment to the group B9 and B10, respectively, and the second number indicates the point of attachment to the group B11 and B12, respectively.

The definitions of M, A3, A4, X1 and X2 contain chemical formulae, such as, for example,

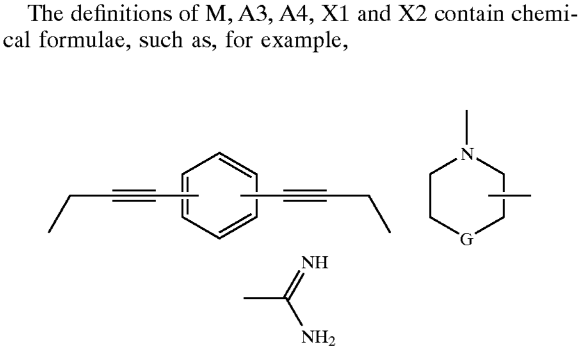

Here, bonds which are unattached on one side mean that the building block is attached at this site to the remainder of the molecule. Bonds which are unattached on both sides mean that this building block has a plurality of sites via which the building block can be attached to the remainder of the molecule.

In the context of this application, the term "terminal nitrogen atom" means in each case a nitrogen atom in the groups designated X1, X2, Y1 and Y2.

If the group X1 or X2 contains only one nitrogen atom, this nitrogen atom is the terminal nitrogen atom.

If the group X1 or X2 contains a plurality of nitrogen atoms, the nitrogen atom which is furthest from the atom by means of which the bond to the group B9 (B11) or B10 (B12) is established is the terminal nitrogen atom.

If the group Y1 or Y2 contains only one ring nitrogen atom, this ring nitrogen atom is the terminal nitrogen atom.

If the group Y1 or Y2 contains a plurality of ring nitrogen atoms, the ring nitrogen atom which is furthest from the atom by means of which the bond to the group B9 or B10 is established is the terminal nitrogen atom.

According to the invention, the direct route between the nitrogen atoms which act as terminal nitrogen atoms in the groups defined as X1 (Y1) or X2 (Y2) is considered to be the number of bonds which is obtained by counting the bonds which represent the shortest possible connection between the terminal nitrogen atoms.

The following example is meant to illustrate the determination of the number of bonds on the direct route between two terminal nitrogen atoms:

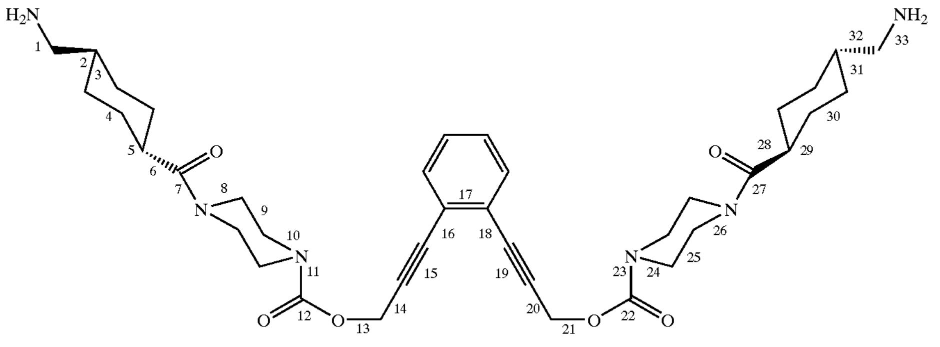

Here, the direct route comprises 33 bonds.

Suitable salts for compounds of the formula I—depending on substitution—ar all acid addition salts or all salts with bases. Particular mention may be made of the pharmacologically acceptable salts of inorganic and organic acids customarily used in pharmacy. Those suitable are, on the one hand, water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are employed in salt preparation—depending on whether a mono- or polybasic acid is concerned and depending on which salt is desired—in an equimolar quantitative ratio or one differing therefrom.

On the other hand, salts with bases are also suitable. Examples of salts with bases which may be mentioned are alkali metal (lithium, sodium, potassium) or calcium, aluminum, magnesium, titanium, ammonium, meglumine or guanidinium salts, where here too the bases are employed in salt preparation in an equimolar quantitative ratio or one differing therefrom.

Pharmacologically unacceptable salts which can be obtained initially as process products, for example in the preparation of the compounds according to the invention on an industrial scale, are converted into pharmacologically acceptable salts by processes known to the person skilled in the art.

It is known to the person skilled in the art that the compounds according to the invention, and also their salts, may contain varying amounts of solvents, for example when they are isolated in crystalline form. The invention therefore also embraces all solvates and in particular all hydrates of the compounds of the formula I, and also all solvates and in particular all hydrates of the salts of the compounds of the formula I.

Compounds of the formula I to be emphasized are those in which

A1 and A2 are identical or different and are —C(O)—, —NH—, —O—, —C(O)—NH—, —NH—C(O)—, —O—C(O)—, —C(O)—O— or a bond, A3 and A4 are identical or different and are —C(O)—, —O—, —NH—, —O—C(O)—, —C(O)—O—, —C(O)—NH—, —NH—C(O)— or a bond, or are selected from the group consisting of

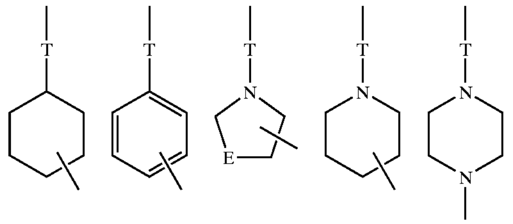

where

E is —O— (oxygen), —S—(sulfur) or —$CH_2$—(methylene) and

T is the group —C(O)— or a bond,

A5 and A6 are identical or different and are —C(O)—, —NH—, —O—, —C(O)—NH—, —NH—C(O)—, —O—C(O), —C(O)—O—, —NH—C(O)—NH— or a bond, M is a central building block selected from the group below

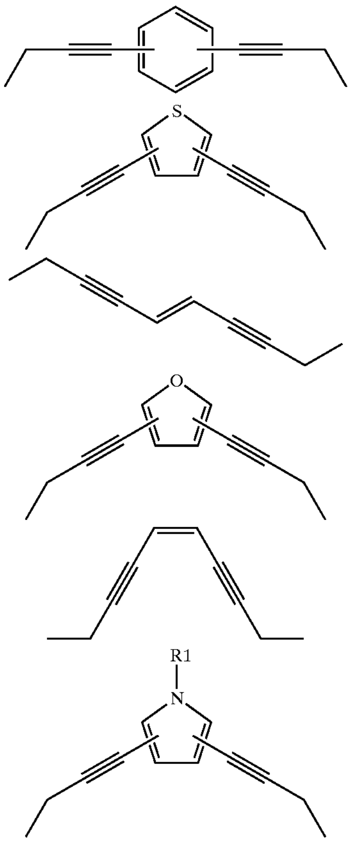

where

R1 is hydrogen, 1–4C-alkyl or 1–4C-alkylcarbonyl,

K1 is —B7—$(C(O))_m$—B9—X1, —B7—$(C(O))_m$—B9—Y1 or —B7—$(C(O))_m$—B9—Z1—B11—X1,

K2 is —B8—$(C(O))_p$—B10—X2, —B8—$(C(O))_p$—B10—Y2 or —B8—$(C(O))_p$—B10—Z2—B12—X2,

B1, B2, B3, B4, B5 and B6 are identical or different and are a bond or 1–4C-alkylene, B7, B8, B9, B10, B11 and B12 are identical or different and are a bond or 1–4C-alkylene, m is 0 or 1, p is 0 or 1, X1 and X2 are identical or different and are selected from the group consisting of

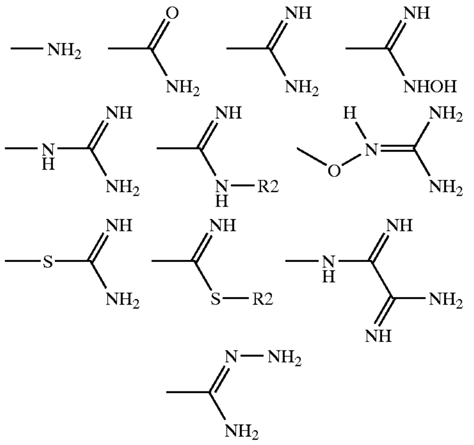

where

R2 is 1–4C-alkyl,

Y1 and Y2 are identical or different and are piperid-4-yl, piperid-3-yl, piperazin-1-yl, piperazin-2-yl, morpholin-2-yl, pyrrolidin-2-yl, pyrrolidin-3-yl, imidazolidin-1-yl, imidazolidin-2-yl, imidazolidin-4-yl, 2-imidazolin-3-yl, 2-imidazolin-2-yl, imidazol-1-yl, imidazol-2-yl, imidazol-4-yl, pyrid-4-yl, pyrid-3-yl, pyridazin-4-yl, pyrimidin-5-yl, pyrimidin-4-yl, indol-3-yl, benzimidazol-4-yl or benzimidazol-5-yl, Z1 and Z2 are identical or different and are 1,4-phenylene, 1,3-phenylene, 1,4-naphthylene, 2,6-naphthylene, 1,4-cyclohexylene, 1,3-cyclohexylene, 1,3-cyclopentylene, 1,4-piperazinylene, 4,1-piperidinylene, 1,4-piperidinylene, 2,5-pyrrolidinylene, 4,2-imidazolidinylene, 2,5-furylene, 2,5-pyrrolylene, 4,2-pyridylene, 5,2-pyridylene, 2,5-indolylene, 2,6-indolylene, 3,5-indolylene, 3,6-indolylene, 3,5-indazolylene, 3,6-indazolylene, 2,6-quinolinylene, 2,5-benzofuranylene or 4,2-thiazolylene, where each arylene, heteroarylene, cycloalkylene, heterocycloalkylene, heteroaryl or heterocycloalkyl may additionally for its part be substituted by one, two or three substituents selected from the group consisting of hydroxyl, halogen, nitro, cyano, amino, 1–4C-alkyl, 1–4C-alkoxy, 1–4C-alkoxycarbonyl, 1–4C-alkylcarbonyloxy, carboxyl or aminocarbonyl, and where on the direct route between the terminal nitrogen atoms 20 to 40, preferably 25 to 40, bonds have to be present, the salts of these compounds, and the N-oxides of the nitrogen-containing heteroaryls, heterocycloalkyls, heteroarylenes and heterocycloalkylenes, and their salts, where all those compounds are excluded in which one or more of the variables B1, B2, B3, B4, B5, B6, B7, B8, B9, B10, B11 or B12 may assume the meaning of a bond, resulting in the direct linkage of two heteroatoms or carbonyl groups.

Compounds of the formula I which are to be particularly emphasized are those in which A1 and A2 are identical or different and are —O—, —C(O)—, —O—C(O)—, —NH—C(O)— or a bond, A3 and A4 are identical or different and are 1,4-piperazinylene, 1,4-piperidinylene, 1,4-cyclohexylene, 1,3-phenylene or a bond, A5 and A6 are identical or different and are —C(O)—, —C(O)—NH—, —NH—C(O)— or —NH—C(O)—NH—, M is a central building block selected from the group below

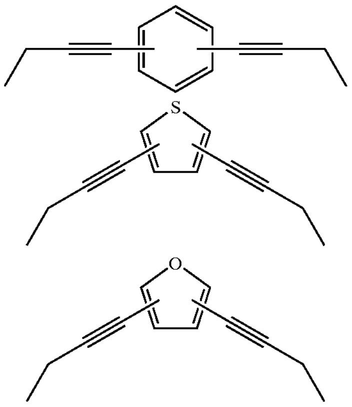

K1 is —B7—(C(O))$_m$—B9—Y1 or —B7—(C(O))$_m$—B9—Z1—B11—X1,

K2 is —B8—(C(O))$_p$—B10—Y2 or —B8—(C(O))$_p$—B10—Z2—B12—X2,

B1 and B2 are identical or different and are a bond or methylene,

B3, B4, B5 and B6 are identical or different and are a bond or 1–3C-alkylene,

B7, B8, B9 and B10 are identical or different and are a bond or 1–4C-alkylene,

B11 and B12 are identical or different and are a bond or methylene, m is 0, p is 0, X1 and X2 are identical or different and are selected from the group consisting of

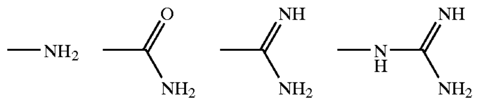

Y1 and Y2 are imidazol-1-yl,

Z1 and Z2 are identical or different and are 5,2-pyridinylene, 6-methyl-5,2-pyridinylene, 4,1-piperidinylene, 3,6-indazolylene, 3,6-indolylene, 1,3-phenylene, 1,4-phenylene, 1,3-cyclohexylene or 1,4-cyclohexylene, and where on the direct route between the terminal nitrogen atoms 20 to 40, preferably 25 to 40, bonds have to be present, the salts of these compounds, and the N-oxides of nitrogen-containing heteroaryls, heteroarylenes and heterocycloalkylenes, and their salts, where all those compounds are excluded in which one or more of the variables B1, B2, B3, B4, B5, B6, B7, B8, B9, B10, B11 or B12 may assume the meaning of a bond, resulting in the direct linkage of two heteroatoms or carbonyl groups.

Preferred compounds of the formula I are those in which

A1 and A2 are identical or different and are —O—, —C(O)—, —O—C(O)—, —NH—C(O)— or a bond, A3 and A4 are identical or different and are 1,4-piperazinylene, 1,4-piperidinylene, 1,4-cyclohexylene, 1,3-phenylene or a bond, A5 and A6 are identical or different and are —C(O)—, —C(O)—NH—, —NH—C(O)— or —NH—C(O)—NH—, M is a central building block selected from the group below

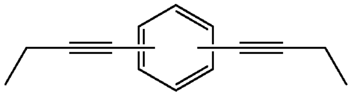

K1 is —B7—(C(O))$_m$—B9—Y1 or —B7—(C(O))$_m$—B9—Z1—B11—X1,

K2 is —B8—(C(O))$_p$—B10—Y2 or —B8—(C(O))$_p$—B10—Z2—B12—X2,

B1 and B2 are identical or different and are a bond or methylene,

B3, B4, B5 and B6 are identical or different and are a bond or 1–3C-alkylene,

B7, B8, B9 and B10 are identical or different and are a bond or 1–4C-alkylene,

B11 and B12 are identical or different and are a bond or methylene, m is 0, p is 0, X1 and X2 are identical or different and are selected from the groups below

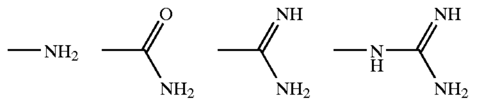

Y1 and Y2 are imidazol-1-yl,

Z1 and Z2 are identical or different and are 5,2-pyridinylene, 6-methyl-5,2-pyridinylene, 4,1-piperidinylene, 3,6-indazolylene, 3,6-indolylene, 1,3-phenylene, 1,4-phenylene, 1,3-cyclohexylene or 1,4-cyclohexylene, and where on the direct route between the terminal nitrogen atoms 20 to 40, preferably 25 to 40, bonds have to be present, the salts of these compounds, and also the N-oxides of the nitrogen-containing heteroaryls, heteroarylenes and heterocycloalkylenes, and their salts, where all those compounds are excluded in which one or more of the variables B1, B2, B3, B4, B5, B6, B7, B88, B9, B10, B11 or B12 may assume the meaning of a bond, resulting in the direct linkage of two heteroatoms or carbonyl groups.

Particularly preferred compounds of the formula I are those in which

A1 and A2 are —O—C(O)—,

A3 and A4 are 1,4-piperazinylene,

A5 and A6 are identical or different and are —C(O)— or —C(O)—NH—,

M is a central building block selected from the groups below

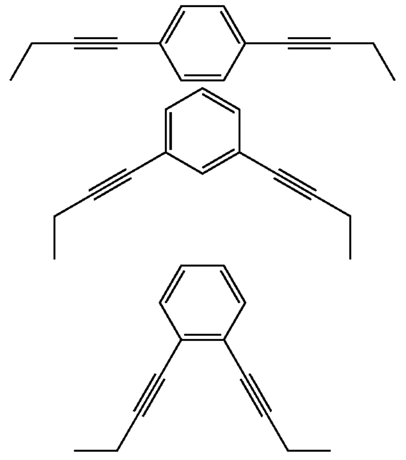

K1 is —B7—(C(O))$_m$—B9—Z1—B11—X1,

K2 is —B8—(C(O))$_p$—B10—Z2—B12—X2,

B1, B2, B3, B4, B5 and B6 are a bond,

B7 and B8 are identical or different and are a bond or methylene,

B9 and B10 are a bond,

B11 and B12 are methylene, m is 0, p is 0,

X1 and X2 are amino,

Z1 and Z2 are identical or different and are 1,4-phenylene or 1,4-cyclohexylene, and the salts of these compounds.

Further particularly preferred compounds of the formula I are 1,2-bis[4-(trans-4-aminomethylcyclohexylcarbonyl)-1-piperazinylcarbonyl-1-oxyprop-2-ynyl]benzene;

1,4-bis[4-(trans-4-aminomethylcyclohexylcarbonyl)-1-piperazinylcarbonyl-1-oxyprop-2-ynyl]benzene;

1,2-bis[4-(4-aminomethylbenzylaminocarbonyl)-1-piperazinylcarbonyl-1-oxyprop-2-ynyl]benzene;

1,3-bis[4-(4-aminomethylbenzylaminocarbonyl)-1-piperazinylcarbonyl-1-oxyprop-2-ynyl]benzene;

and the salts of these compounds.

An embodiment (embodiment a) of the compounds of the formula I are those in which —B1—A1—B3—A3—B5—A5— and —B2—A2—B4—A4—B6—A6— are identical or different and are selected from the groups below

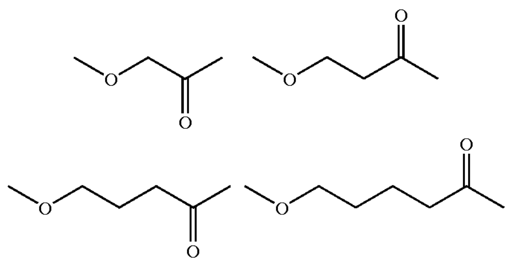

-continued

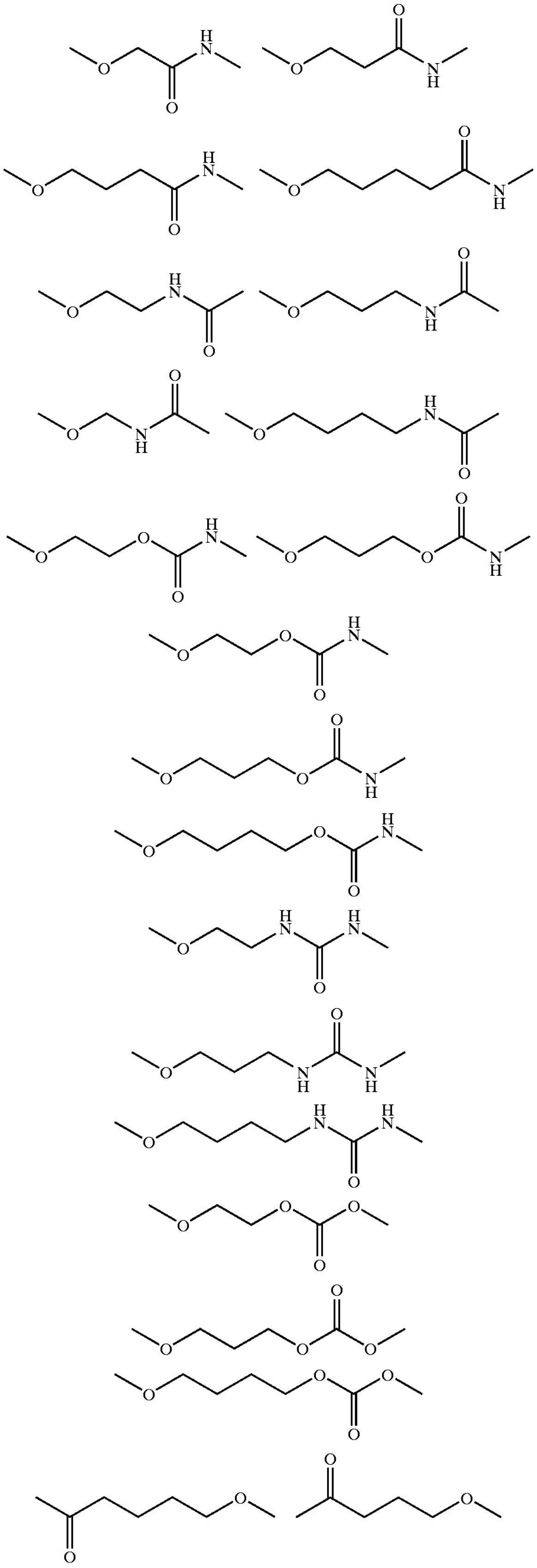

-continued
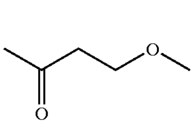 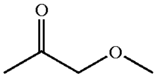
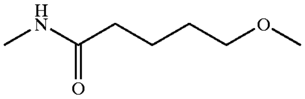
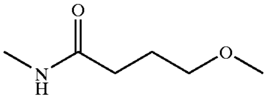 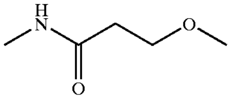
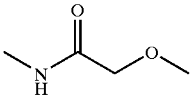 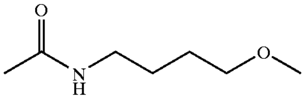
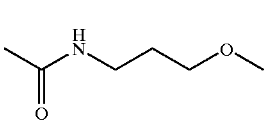 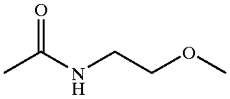
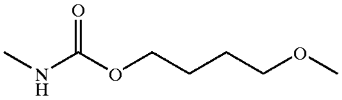
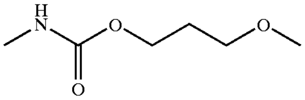 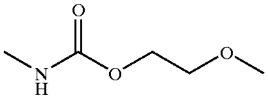
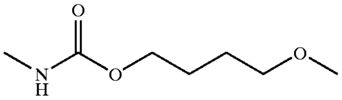
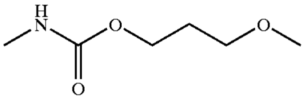
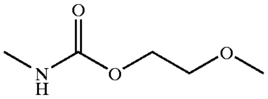
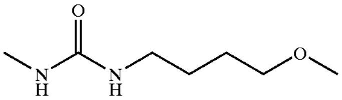
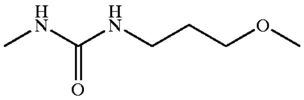 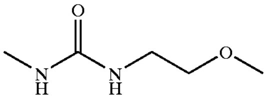
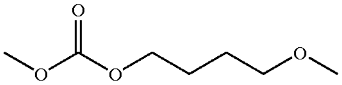
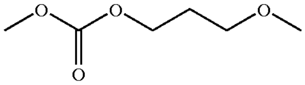 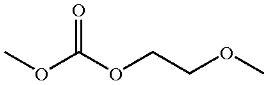
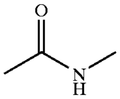 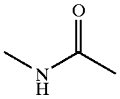 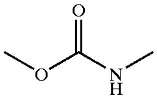 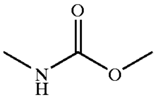
-continued
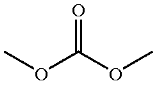 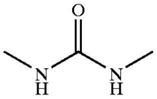 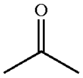
M is a central building block selected from the groups below
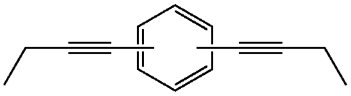
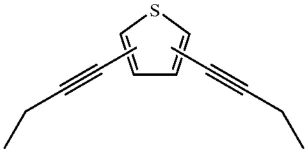
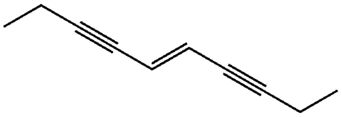
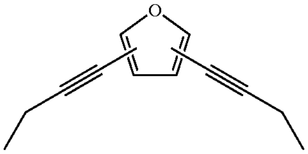
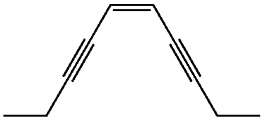
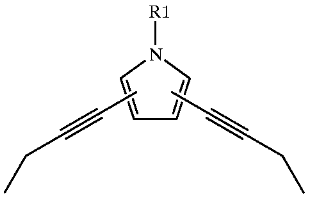
where
R1 is hydrogen, 1–4C-alkyl or 1–4C-alkylcarbonyl,
K1 is —B7—(C(O))$_m$—B9—X1, —B7—(C(O))$_m$—B9—Y1 or —B7—(C(O))$_m$—B9—Z1—B11—X1,
K2 is —B8—(C(O))$_p$—B10—X2, —B8—(C(O))$_p$—B10—Y2 or —B8—(C(O))$_p$—B10—Z2—B12—X2,
B7, B8, B9, B10, B 11 and B12 are identical or different and are a bond or 1–4C-alkylene,
m is 0 or 1,
p is 0 or 1,
X1 and X2 are identical or different and are selected from the groups below
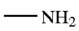 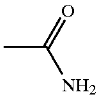 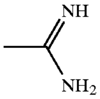 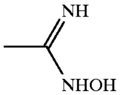
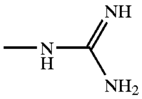 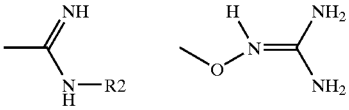

-continued

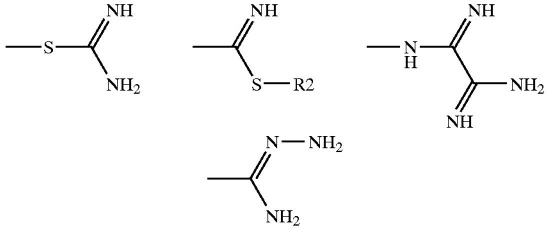

where

R2 is 1–4C-alkyl,

Y1 and Y2 are identical or different and are piperid-4-yl, piperid-3-yl, piperazin-1-yl, piperazin-2-yl, morpholin-2-yl, pyrrolidin-2-yl, pyrrolidin-3-yl, imidazolidin-1-yl, imidazolidin-2-yl, imidazolidin-4-yl, 2-imidazolin-3-yl, 2-imidazolin-2-yl, imidazol-1-yl, imidazol-2-yl, imidazol-4-yl, pyrid-4-yl, pyrid-3-yl, pyridazin-4-yl, pyrimidin-5-yl, pyrimidin-4-yl, indol-3-yl, benzimidazol-4-yl or benzimidazol-5-yl, Z1 and Z2 are identical or different and are 1,4-phenylene, 1,3-phenylene, 1,4-naphthylene, 2,6-naphthylene, 1,4-cyclohexylene, 1,3-cyclohexylene, 1,3cyclopentylene, 1,4-piperazinylene, 4,1-piperidinylene, 1,4-piperidinylene, 2,5-pyrrolidinylene, 4,2-imidazolidinylene, 2,5-furylene, 2,5-pyrrolylene, 4,2-pyridylene, 5,2-pyridylene, 2,5-indolylene, 2,6-indolylene, 3,5-indolylene, 3,6-indolylene, 3,5-indazolylene, 3,6-indazolylene, 2,6-quinolinylene, 2,5-benzofuranylene or 4,2-thiazolylene, where each arylene, heteroarylene, cycloalkylene, heterocycloalkylene, heteroaryl or heterocycloalkyl may additionally for its part be substituted by one, two or three substituents selected from the group consisting of hydroxyl, halogen, nitro, cyano, amino, 1–4C-alkyl, 14C-alkoxy, 14C-alkoxycarbonyl, 14C-alkylcarbonyloxy, carboxyl or aminocarbonyl, and where on the direct route between the terminal nitrogen atoms 20 to 33 bonds have to be present, the salts of these compounds, and also the N-oxides of the nitrogen-containing heteroaryls, heterocycloalkyls, heteroarylenes and heterocycloalkylenes, and their salts, where all those compounds are excluded in which one or more of the variables B7, B8, B9, B10, B11 or B12 may assume the meaning of a bond, resulting in the direct linkage of two heteroatoms or carbonyl groups.

Compounds of the formula I of the embodiment a which are to be emphasized are those in which —B1—A1—B3—A3—B5—A5— and —B2—A2—B4—A4—B6—A6— are identical or different and are selected from the groups below

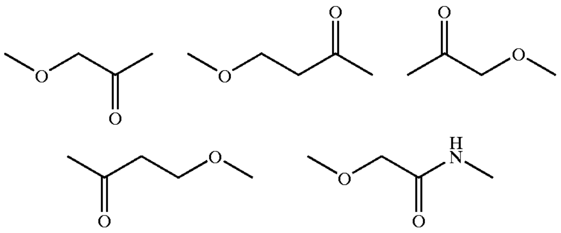

-continued

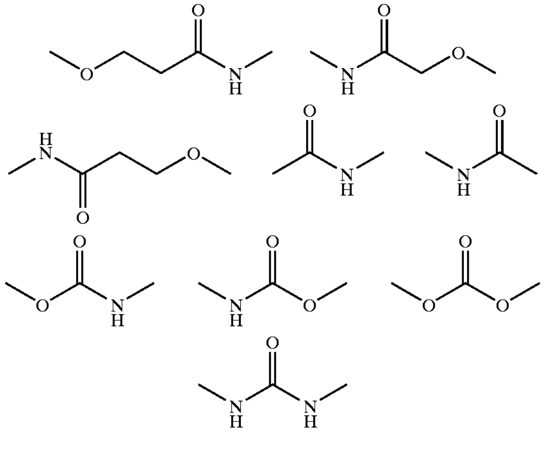

M is a central building block selected from the groups below

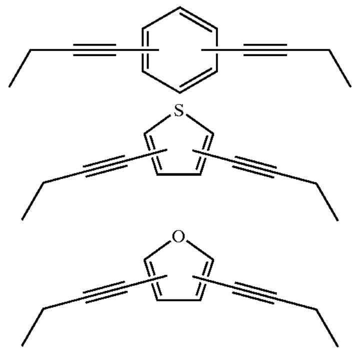

K1 is —B7—(C(O))$_m$—B9—Y1 or —B7—(C(O))$_m$—B9—Z1—B11—X1,

K2 is —B8—(C(O))$_p$—B10—Y2 or —B8—(C(O))$_p$—B10—Z2—B12—X2,

B7, B8, B9, B10, B11 and B12 are identical or different and are a bond or 1–2C-alkylene, m is 0, p is 0, X1 and X2 are identical or different and are selected from the groups below

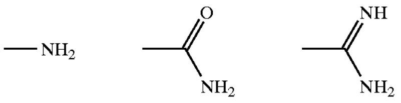

Y1 and Y2 imidazol-1-yl,

Z1 and Z2 are identical or different and are 5,2-pyridinylene, 6-methyl-5,2-pyridinylene, 4,1-piperidinylene, 3,6-indazolylene, 3,6-indolylene, 1,3-phenylene, 1,4-phenylene, 1,3-cyclohexylene or 1,4-cyclohexylene, and where on the direct route between the terminal nitrogen atoms 20 to 33 bonds have to be present, the salts of these compounds, and also the N-oxides of the nitrogen-containing heteroaryls, heteroarylenes and heterocycloalkylenes, and their salts.

Compounds of the formula I of the embodiment a which are to be particularly emphasized are those in which —B1—A1—B3—A3—B5—A5— and —B2—A2—B4—A4—B6—A6— are identical or different and are selected from the groups below

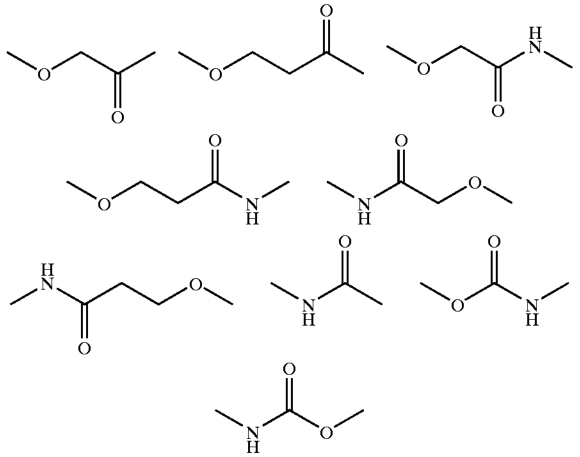

M is a central building block selected from the groups below

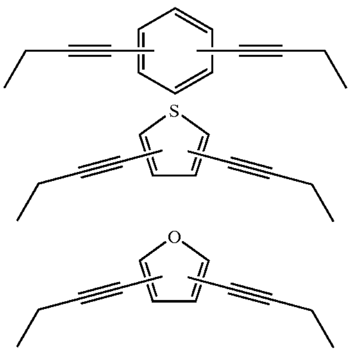

K1 is —B7—(C(O))$_m$—B9—Z1—B11—X1,

K2 is —B8—(C(O))$_p$—B10—Z2—B12—X2,

B7 and B8 are identical or different and are 1–2C-alkylene,

B9 and B10 are identical or different and are a bond or 1–2C-alkylene,

B11 and B12 are identical or different and are 1–2C-alkylene, m is 0, p is 0,

X1 and X2 are amino,

Z1 and Z2 are identical or different and are 1,3-phenylene, 1,4-phenylene, 1,3-cyclohexylene or 1,4-cyclohexylene, and where on the direct route between the terminal nitrogen atoms 20 to 33 bonds have to be present, and the salts of these compounds.

Preferred compounds of the formula I of the embodiment a are those in which

—B1—A1—B3—A3—B5—A5— and —B2—A2—B4—A4—B6—A6— are identical or different and are selected from

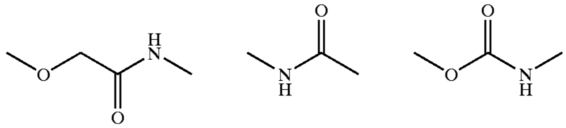

M is a central building block selected from the group below

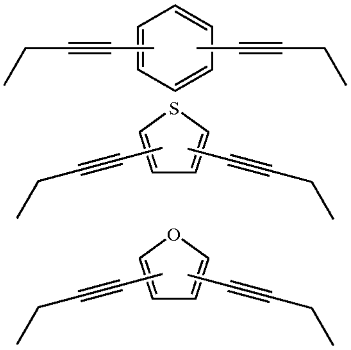

K1 is —B7—(C(O))$_m$—B9—Z1—B11—X1,

K2 is —B8—(C(O))$_p$—B10—Z2—B12—X2,

B7 and B8 are methylene,

B9 and B10 are identical or different and are a bond or methylene,

B11 and B12 are methylene, m is 0, p is 0,

X1 and X2 are amino,

Z1 and Z2 are identical or different and are 1,4-phenylene or 1,3-phenylene, and the salts of these compounds.

Particularly preferred compounds of the formula I of the embodiment a are 1,3-Bis-(4-aminomethylbenzylaminocarbonyl-1-oxyprop-2-ynyl)-benzene;

1,2-Bis-(4-aminomethylbenzylaminocarbonyl-1-oxyprop-2-ynyl)-benzene;

3,4-Bis-(4-aminomethylbenzylaminocarbonyl-1-oxyprop-2-ynyl)-thiophene;

2,5-Bis-(4-aminomethylbenzylaminocarbonyl-1-oxyprop-2-ynyl)-furan;

2,5-Bis-(3-aminomethylbenzylaminocarbonyl-1-oxyprop-2-ynyl)-furan;

3,4-Bis-(3-aminomethylbenzylaminocarbonyl-1-oxyprop-2-ynyl)-thiophene;

1,4-Bis-(4-aminomethylbenzylaminocarbonylmethyl-1-oxyprop-2-ynyl)-benzene;

1,3-Bis-(4-aminomethylbenzylaminocarbonylmethyl-1-oxyprop-2-ynyl)-benzene;

1,4-Bis-(4-aminomethylbenzylcarbonyl-1-aminoprop-2-ynyl)-benzene;

1,2-Bis-(4-aminomethylbenzylcarbonyl-1-aminoprop-2-ynyl)-benzene;

1,4-Bis-(4-aminomethylphenylethylcarbonyl-1-aminoprop-2-ynyl)-benzene;

and the salts of these compounds.

The compounds of the formula I are constructed from a large number of building blocks (M, A1, A2, A3, A4, A5, A6, B1, B2, B3, B4, B5, B6, B7, B8, B9, B10, B11, B12, X1, X2, Y1, Y2, Z1 and Z2). In principle, they can be synthesized starting with any of these building blocks. If the compounds of the formula I are constructed largely symmetrically, it is favorable to start the synthesis with the central building block M, whereas in the case of predominantly asymmetrical compounds of the formula I a synthesis starting with one of the end groups K1 or K2 may be advantageous.

Here, the building blocks are linked using always the same pattern, known per se to the person skilled in the art.

It is known to the person skilled in the art that the compounds of the formula I can either be synthesized building block by building block, or by initially constructing relatively large fragments consisting of several individual building blocks, which can then be joined to give the complete molecule.

Owing to the meanings which the individual building blocks of the compounds of the formula I can assume, amino [—NH—], ether [—O—], thioether [—S—], keto [—C(O)—], sulfonyl [—$S(O)_2$—], ester [—C(O)O—, —O—C(O)—], amide [—C(O)—NH—, —NH—C(O)—], sulfonamide [—$SO_2$—NH—, —NH—$SO_2$—], carbamate [—NH—C(O)—O—, —O—C(O)—NH—], carbamide [—NH—C(O)—NH—] or carbonate bridges [—O—C(O)—O—] are present in the compounds of the formula I.

How to prepare such bridges is known per se to the person skilled in the art; suitable methods and starting materials for their preparation are described, for example, in March, Advanced Organic Chemistry, Reactions, Mechanisms and Structure, Third Edition, 1985, John Wiley & Sons.

Ether and thioether bridges can be prepared, for example, by the method of Williamson.

Keto bridges can be introduced, for example, as a component of relatively large building blocks, such as, for example, 1,3-dichloroacetone.

Sulfonyl bridges can be obtained, for example, by oxidation of thioether bridges.

A large number of methods are known for synthesizing ester bridges. Mention may be made here, by way of example, of the reaction of acids with alcohols, preferably using $H_2SO_4$ or p-toluenesulfonic acid as catalyst; or with the addition of a water-extracting agent, such as a molecular sieve or a carbodiimide. The reaction of acid chlorides with alcohols may also be mentioned at this point.

There is also a large number of known methods for preparing amide bridges. An example which may be mentioned here is the reaction of acyl chlorides with primary or secondary amines. Furthermore, reference is also made to all the methods which have been developed for peptide chemistry. Accordingly, it is possible to construct sulfonamide bridges from sulfonyl chlorides and primary or secondary amines.

Carbamate bridges can be prepared, for example, by reacting chloroformates with amines. The chloroformates for their part can be synthesized from alcohols and phosgene. A further variant for constructing carbamate bridges is the addition of alcohols to isocyanates.

Similarly to the carbamate bridges, it is possible to prepare carbonate bridges starting from chloroformates, by reaction with alcohols (instead of amines).

Carbamide bridges can be prepared, for example, by reacting isocyanates with amines.

The preparation of compounds of the formula I is shown in an exemplary manner using the reaction schemes below. Reaction scheme 1 shows the preparation of some exemplary central building blocks. Reaction schemes 2 to 8 show the preparation of exemplary end products. Other compounds of the formula I can be prepared analogously, or by using the abovementioned methods known per se to the person skilled in the art.

Reaction scheme 1:

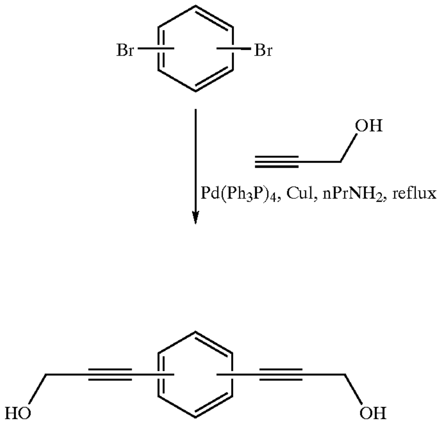

| | | |
|---|---|---|
| A7 | 1,2- | (Tetrabedron Lett. 1987, 28 (48), 5981–5984) |
| A5 | 1,3- | |
| A6 | 1,4- | |

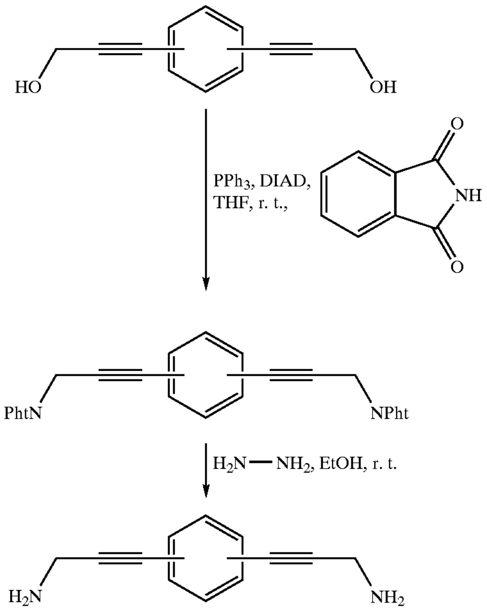

| | |
|---|---|
| A24 | 1,2- |
| A23 | 1,4- |

-continued
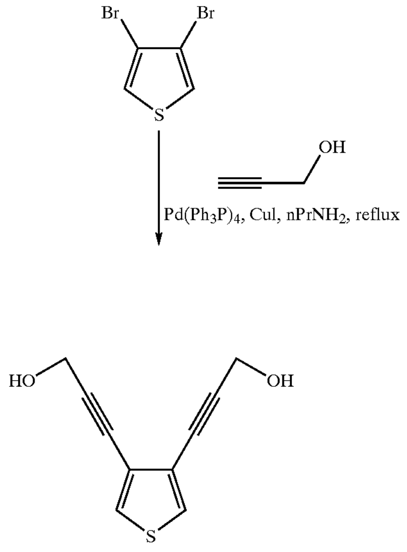
| | |
|---|---|
| A27 | 3,4- |
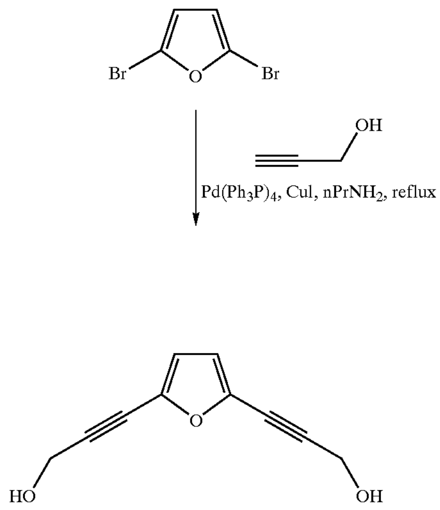
| | |
|---|---|
| A28 | 2,5- |
Reaction scheme 2:
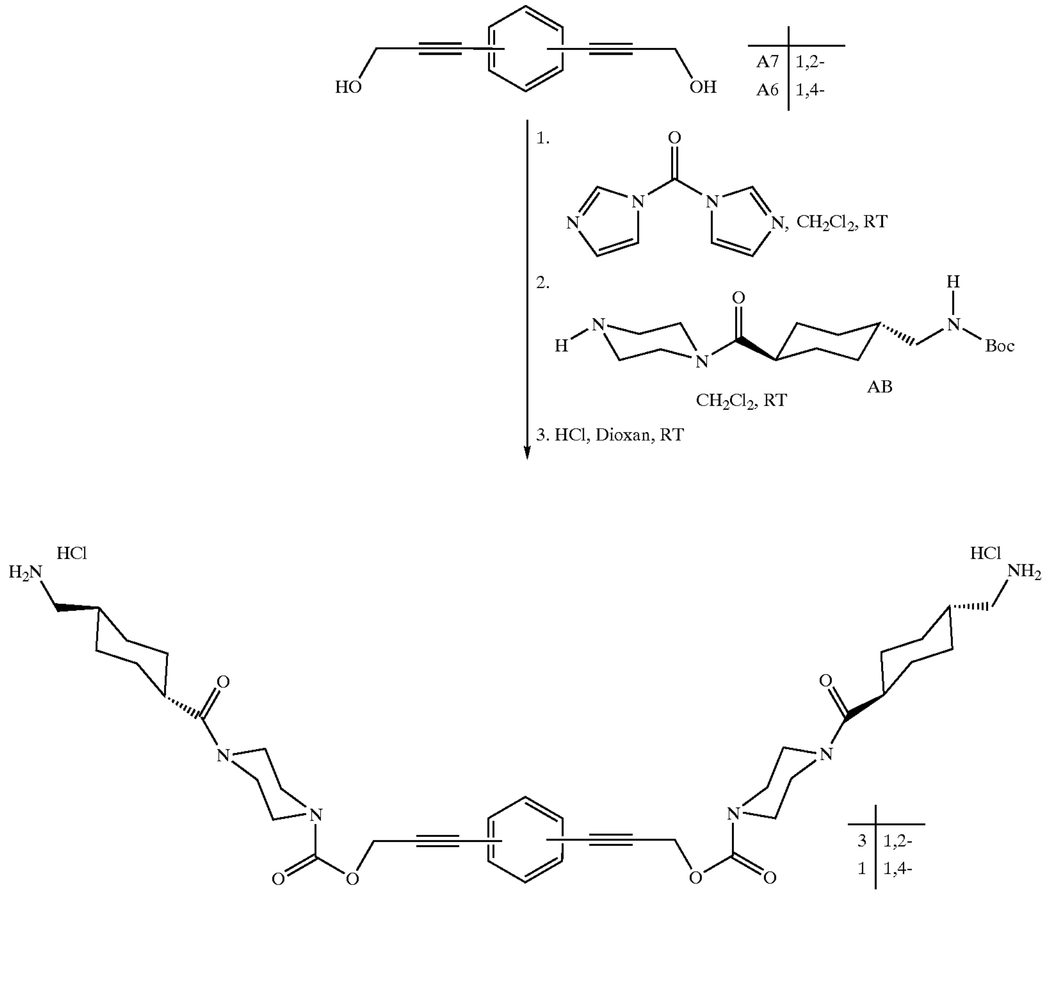

Reaction scheme 3:
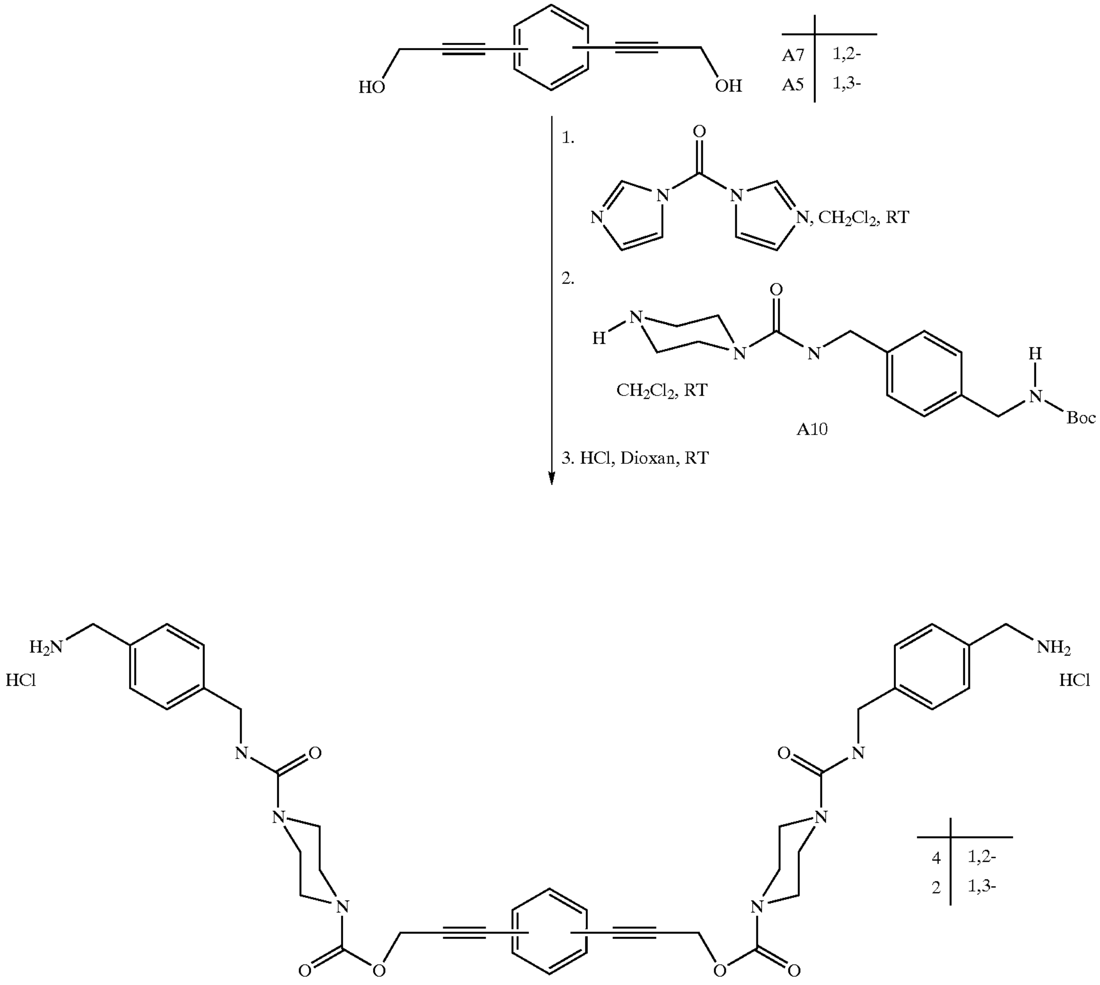
Reaction scheme 4:
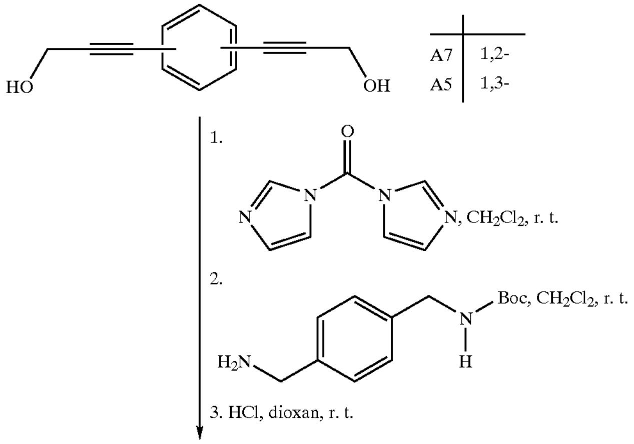

-continued
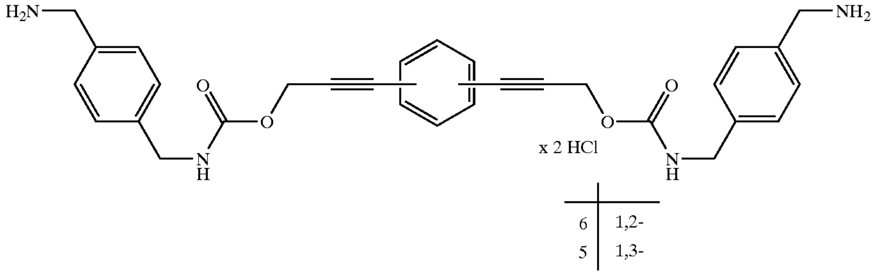
Reaction scheme 5:
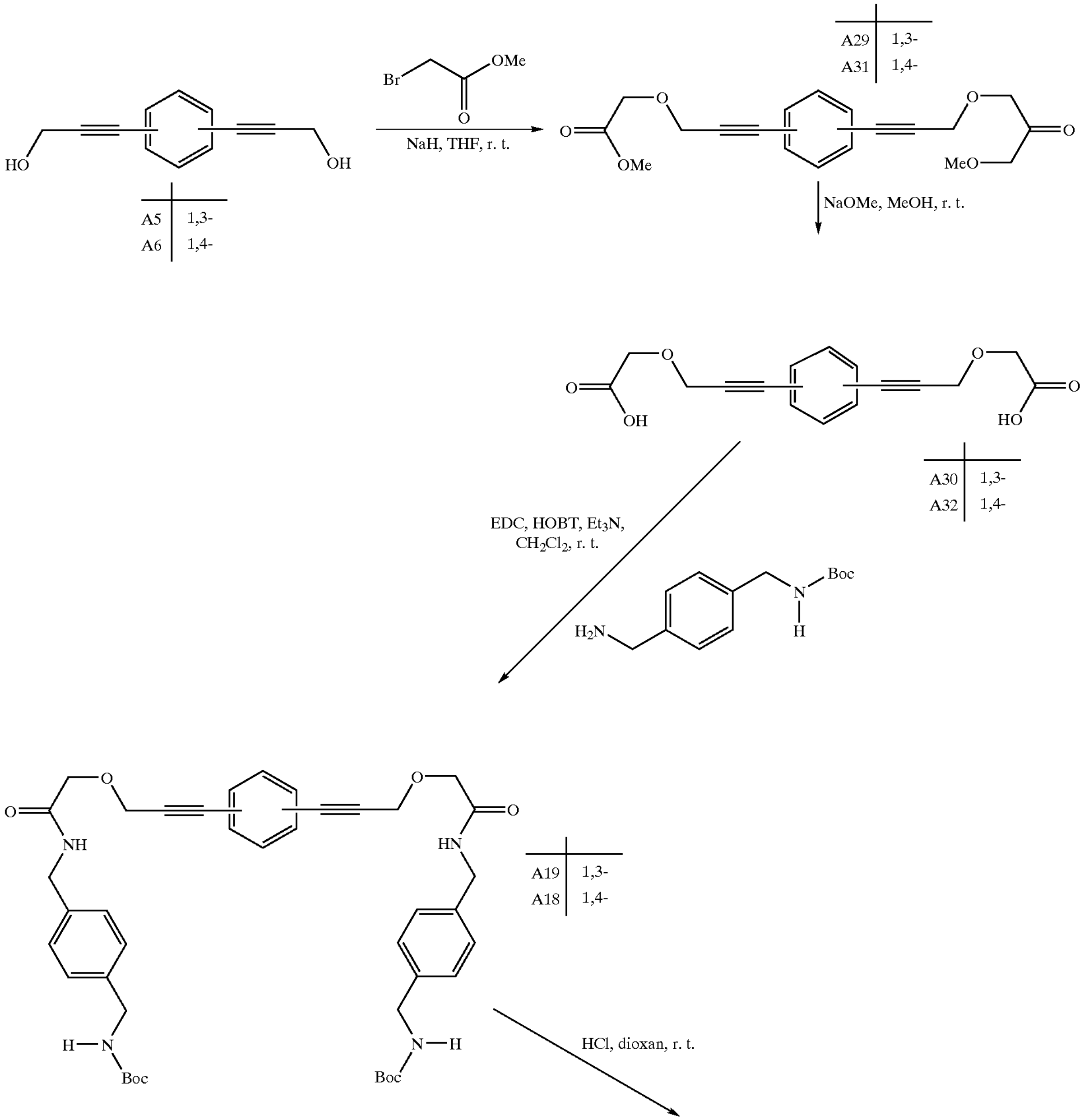

-continued
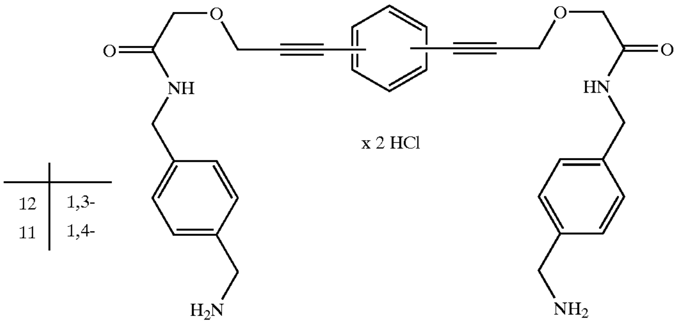
| | |
|---|---|
| 12 | 1,3- |
| 11 | 1,4- |
Reaction scheme 6:
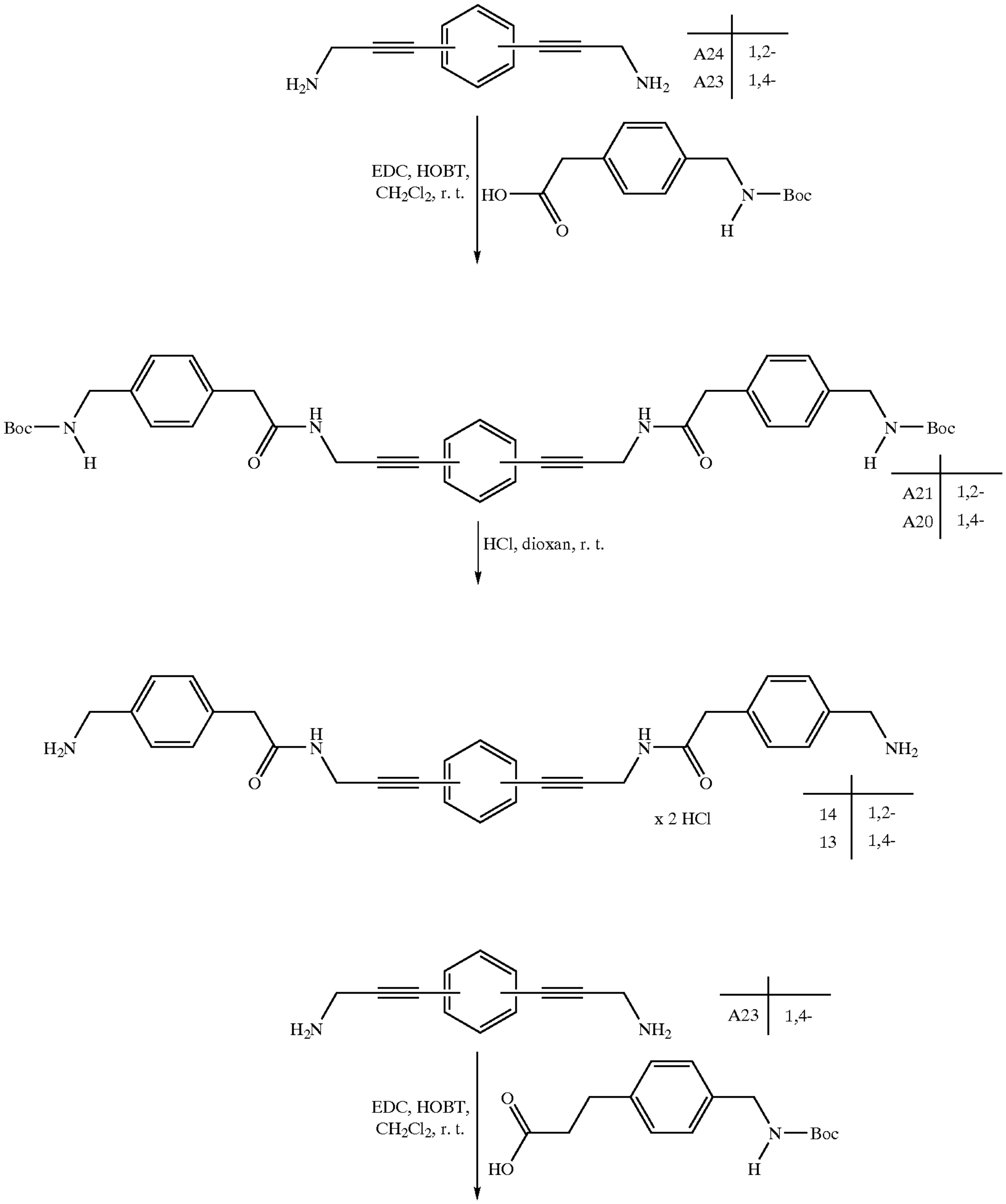
| | |
|---|---|
| A24 | 1,2- |
| A23 | 1,4- |
| | |
|---|---|
| A21 | 1,2- |
| A20 | 1,4- |
| | |
|---|---|
| 14 | 1,2- |
| 13 | 1,4- |
| | |
|---|---|
| A23 | 1,4- |

-continued
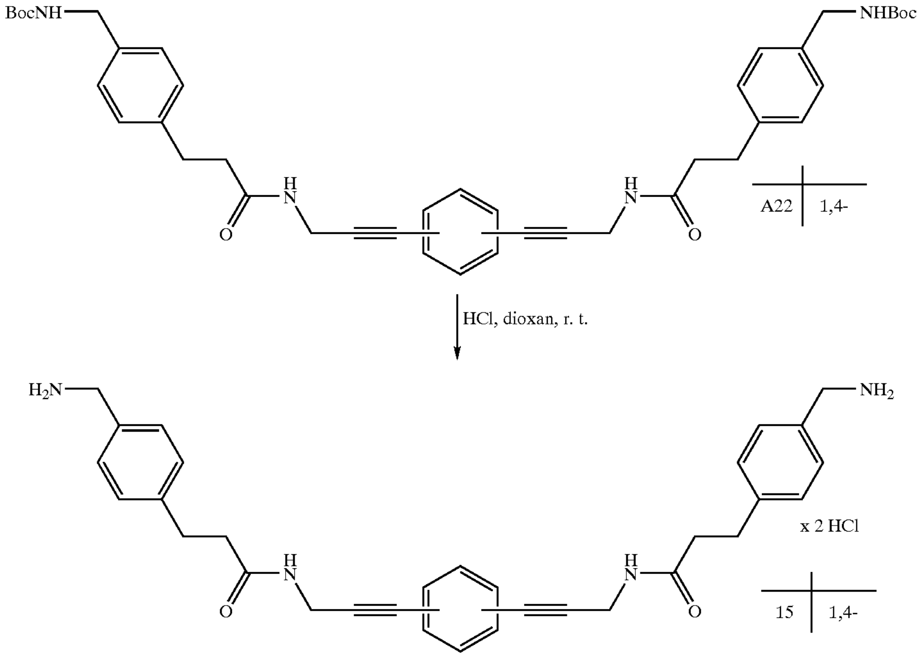
Reaction scheme 7:
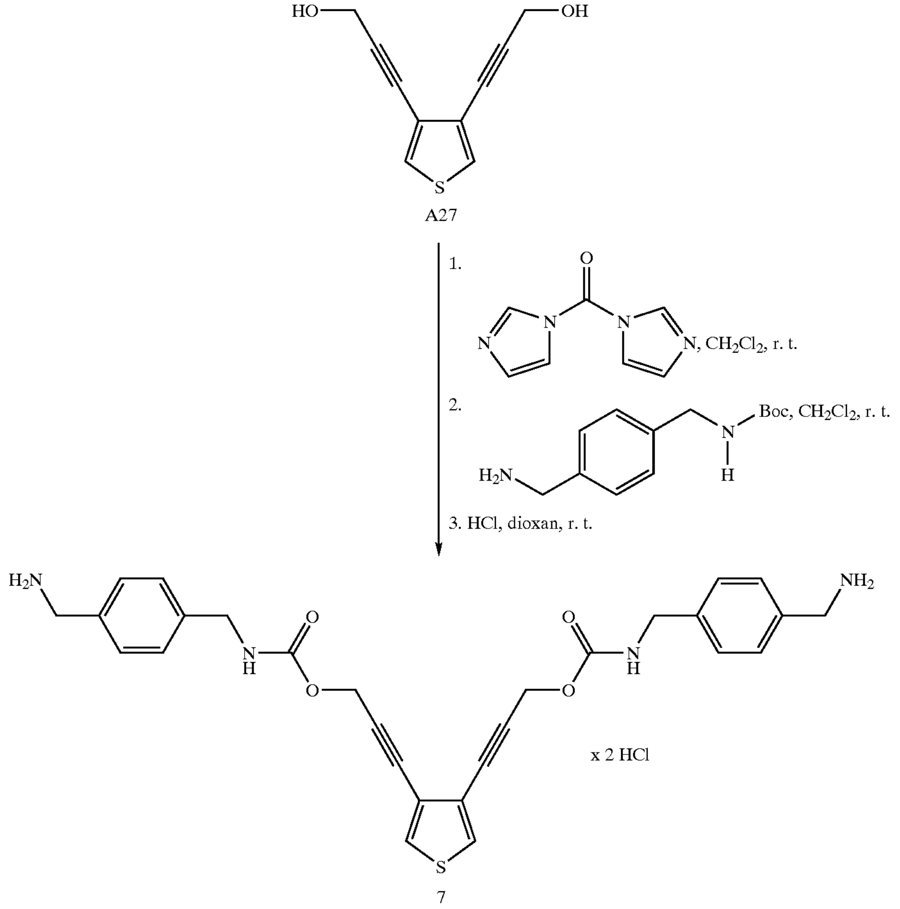

-continued
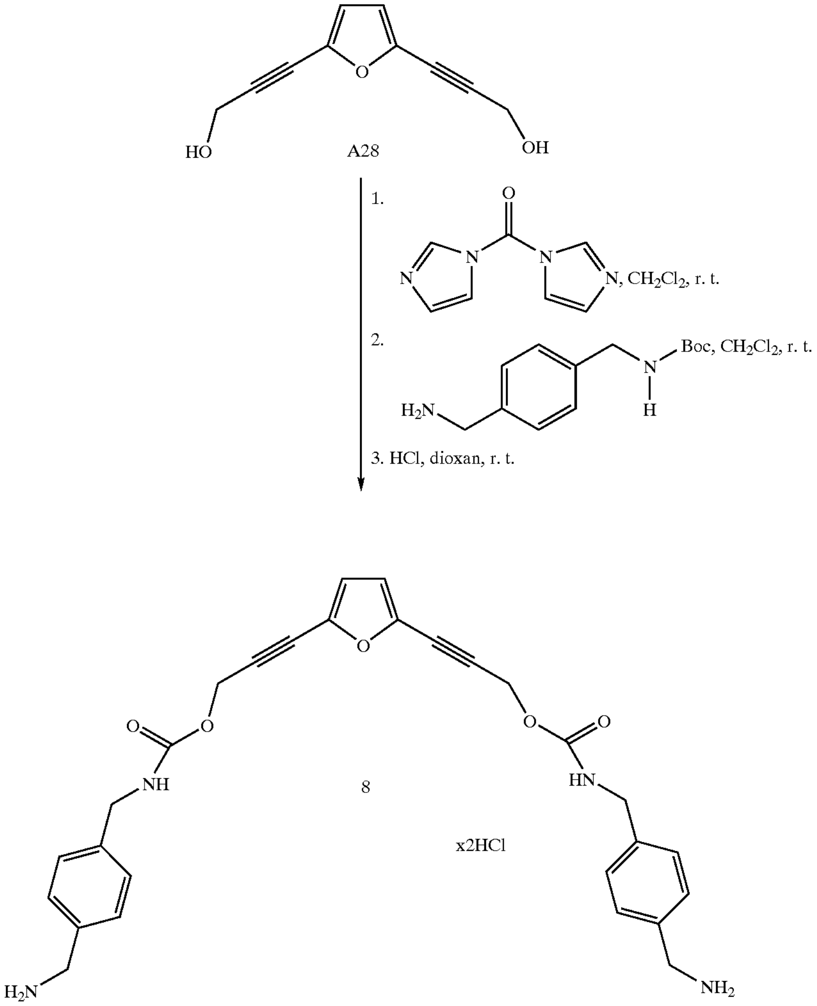
A28
8
x2HCl
Reaction scheme 8:
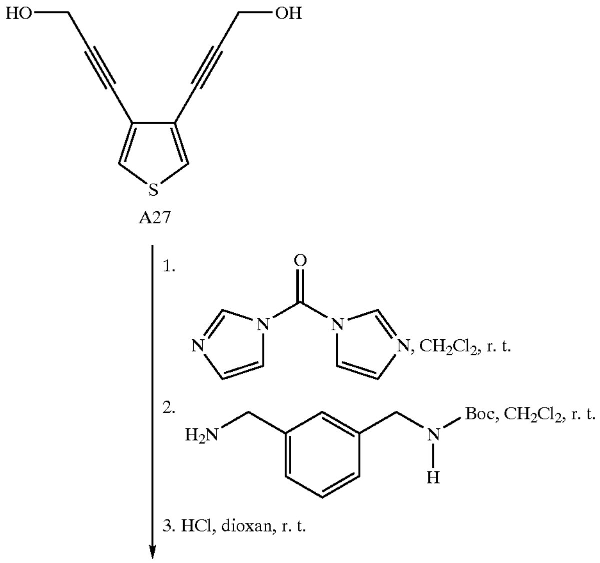
A27

-continued

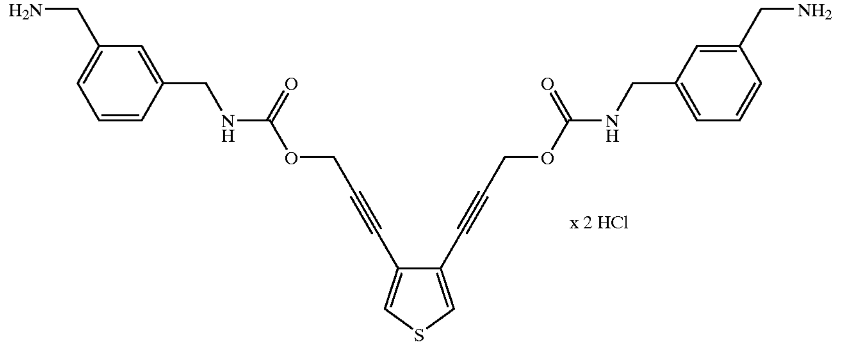

10

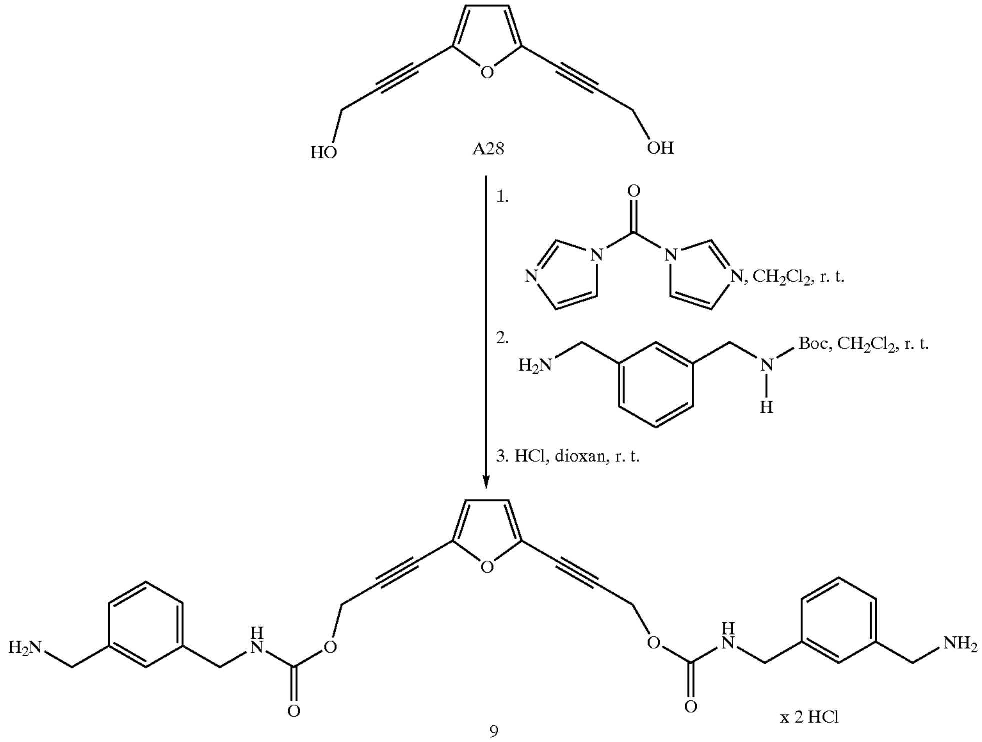

9

It is also possible to convert compounds of the formula I by derivatization into other compounds of the formula I. Thus, for example, compounds of the formula I having a nitrogen-containing heteroaryl, heteroarylene, heterocycloalkyl or heterocycloalkylene building block can be converted by oxidation into the corresponding N-oxides.

The N-oxidation is carried out in a manner which is likewise known to the person skilled in the art, for example using hydrogen peroxide in methanol or m-chloroperoxybenzoic acid in dichloromethane at room temperature. Which reaction conditions are required in the particular case for carrying out the process is known to the person skilled in the art owing to his expert knowledge.

It is furthermore known to the person skilled in the art that if there are a number of reactive centers on a starting material or intermediate, it may be necessary to block one or more reactive centers temporarily by protective groups in order to allow a reaction to proceed specifically at the desired reaction center. A detailed description of the use of a large number of proven protective groups is found, for example, in T. W. Greene, Protective Groups in Organic Synthesis, John Wiley & Sons, 1991.

The isolation and purification of the substances according to the invention is carried out in a manner known per se, for example by distilling off the solvent under reduced pressure and recrystallizing the resulting residue from a suitable solvent or subjecting it to one of the customary purification methods, such as, for example, column chromatography on a suitable support material.

Salts are obtained by dissolving the free compound in a suitable solvent (for example a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low-molecular-weight aliphatic alcohol, such as ethanol or isopropanol) which contains the desired acid or base, or to which the desired acid or base is then added. The salts are obtained by filtering, reprecipitating, precipitating with a nonsolvent for the addition salt or by evaporating the solvent. Salts obtained can be converted by alkalization or by acidification into the free compounds, which in turn can be converted into salts. In this way, pharmacologically unacceptable salts can be converted into pharmacologically acceptable salts.

The examples below serve to illustrate the invention in more detail without restricting it. Likewise, further compounds of the formula I, whose preparation is not explicitly described, can be prepared in an analogous manner or in a manner familiar per se to the person skilled in the art using customary process techniques.

In the examples below, the abbreviation RT stands for room temperature, h for hours, min. for minutes, Tol for toluene, Ac for acetone, calc. for calculated, EDC for N'-(3-dimethylaminopropyl)-N-ethylcarbodiimide), DEAD for diethyl azodicarboxylate, HOBT for 1-hydroxy-1H-benzotriazole, TLC for thin-layer chromatography and MS for mass spectrometry. The compounds mentioned in the examples and their salts are the preferred subject of the invention.

EXAMPLES

End Products:

General Procedure

A solution of the particular Boc-protected bivalent compound (A1–A4, A12–A22; 1.0 mmol) in dioxane (9 ml) is admixed with a saturated solution of HCl in dioxane (5 ml, 22.5 mmol) and stirred at RT for 2–6 h. The resulting precipitate is filtered off under an $N_2$ atmosphere and washed first with dioxane (2×5 ml) and then with diethyl ether (3×5 ml). Drying under reduced pressure gives the title compounds (end products 1–15) as colorless solids.

1. 1,4-Bis[4-(trans-4-aminomethylcyclohexylcarbonyl)-1-piperazinylcarbonyl-1-oxyprop-2-ynyl]benzene Dihydrochloride MS: calc.: $C_{38}H_{52}N_6O_6$ (688.86), found.: [$MH^+$] 689.3

2. 1,3-Bis[4-(4-aminomethylbenzylaminocarbonyl)-1-piperazinylcarbonyl-1-oxyprop-2-ynyl]-benzene Dihydrochloride MS: calc.: $C_{40}H_{46}N_8O_6$ (734.86), found: [$MH^+$] 735.2

3. 1,2-Bis[4-(trans-4-aminomethylcyclohexylcarbonyl)-1-piperazinylcarbonyl-1-oxyprop-2-ynyl]benzene Dihydrochloride MS: calc.: $C_{38}H_{52}N_6O_6$ (688.86), found: [$MH^+$] 689.2

4. 1,2-Bis[4-(4-aminomethylbenzylaminocarbonyl)-1-piperazinylcarbonyl-1-oxyprop-2-ynyl]-benzene Dihydrochloride MS: calc.: $C_{40}H_{46}N_8O_6$ (734.86), found: [$MH^+$] 735.2

5. 1,3-Bis-(4-aminomethylbenzylaminocarbonyl-1-oxyprop-2-ynyl)-benzene Dihydrochloride MS: calc.: $C_{30}H_{30}N_4O_4$ (510,60), found: [$MH^+$] 511,0

6. 1,2-Bis-(4-aminomethylbenzylaminocarbonyl-1-oxyprop-2-ynyl)-benzene Dihydrochloride MS: calc.: $C_{30}H_{30}N_4O_4$ (510,60), found: [$MH^+$] 511,0

7. 3,4-Bis-(4-aminomethylbenzylaminocarbonyl-1-oxyprop-2-ynyl)-thiophene Dihydrochloride MS: calc.: $C_{28}H_{28}N_4O_4S$ (516,60), found: [$MH^+$] 517,0

8. 2,5-Bis-(4-aminomethylbenzylaminocarbonyl-1-oxyprop-2-ynyl)-furan Dihydrochloride MS: calc.: $C_{28}H_{28}N_4O_5$ (500,60), found: [$MH^+$] 501,0

9. 2,5-Bis-(3-aminomethylbenzylaminocarbonyl-1-oxyprop-2-ynyl)-furan Dihydrochloride MS: calc.: $C_{28}H_{28}N_4O_5$ (500,60), found: [$MH^+$] 501,0

10. 3,4-Bis-(3-aminomethylbenzylaminocarbonyl-1-oxyprop-2-ynyl)-thiophene Dihydrochloride MS: calc.: $C_{28}H_{28}N_4O_4S$ (516,60), found: [$MH^+$] 517,0

11. 1,4-Bis-(4-aminomethylbenzylaminocarbonylmethyl-1-oxyprop-2-ynyl)-benzene Dihydrochloride MS: calc.: $C_{32}H_{34}N_4O_4$ (538,38), found: [$MH^+$] 539,1

12. 1,3-Bis-(4-aminomethylbenzylaminocarbonylmethyl-1-oxyprop-2-ynyl)-benzene Dihydrochloride MS: calc.: $C_{32}H_{34}N_4O_4$ (538,38), found: [$MH^+$] 539,1

13. 1,4-Bis-(4-aminomethylbenzylcarbonyl-1-aminoprop-2-ynyl)-benzene Dihydrochloride MS: calc.: $C_{30}H_{30}N_4O_2$ (478,84), found: [$MH^+$] 479,1

14. 1,2-Bis-(4-aminomethylbenzylcarbonyl-1-aminoprop-2-ynyl)-benzene Dihydrochloride MS: calc.: $C_{30}H_{30}N_4O_2$ (478,84), found: [$MH^+$] 479,1

15. 1,4-Bis-(4-aminomethylphenylethylcarbonyl-1-aminoprop-2-ynyl)-benzene Dihydrochloride MS: calc.: $C_{32}H_{34}N_4O_2$ (506,65), found: [$MH^+$] 507,1

Starting Materials:

A1. 1,4-Bis[4-(trans-4-N-tert-butoxycarbonylaminomethylcyclohexylcarbonyl)-1-piperazinylcarbonyl-1-oxyprop-2-ynyl]benzene A solution of 3-[4-(3-hydroxyprop-1-ynyl)phenyl]prop-2-yn-1-ol (A6, 0.4 g, 2.14 mmol) in absolute $CH_2Cl_2$ (10 ml) is admixed with N,N-carbonyldiimidazole (1.04 g, 6.42 mmol) and stirred at RT for 0.5 h. The reaction solution is diluted with $CH_2Cl_2$ (10 ml) and extracted with a semisaturated aqueous NaCl solution (20 ml). The organic phase is dried over $MgSO_4$, filtered off and concentrated under reduced pressure. The resulting residue is taken up in absolute $CH_2Cl_2$ (10 ml), trans-4-N-tert-butoxycarbonylaminomet-1-piperazine (A8, 1.53 g, 4.7 mmol) is added and the mixture is stirred at RT overnight. The reaction solution is diluted with $CH_2Cl_2$ (10 ml) and extracted with a semisaturated aqueous NaCl solution (20 ml). The organic phase is dried over $MgSO_4$, filtered off and concentrated under reduced pressure. Further purification is carried out by chromatography [Tol/Ac (7:3)] over a silica gel column. This gives the title compound (1.67 g) as a colorless solid. TLC, silica gel (glass plates), [toluene/acetone (7:3)], $R_f$=0.33.

MS: calc.: $C_{48}H_{68}N_6O_{10}$ (889.1), found: [$MH^+$] 889.0; [$MNa^+$] 911.2

A2. 1,3-Bis[4-(4-N-tert-butoxycarbonylaminomethylbenzylaminocarbonyl)-1-piperazinyl-carbonyl-1-oxyprop-2-ynyl]benzene A solution of 3-[3-(3-hydroxyprop-1-ynyl)phenyl]prop-2-yn-1-ol (A5, 0.4 g, 2.14 mmol) in absolute $CH_2Cl_2$ (10 ml) is admixed with N,N-carbonyldiimidazole (1.04 g, 6.42 mmol) and stirred at RT for 0.5 h. The reaction solution is diluted with $CH_2Cl_2$ (10 ml) and extracted with a semisaturated aqueous NaCl solution (20 ml). The organic phase is dried over $MgSO_4$, filtered off and concentrated under reduced pressure. The resulting residue is taken up in absolute $CH_2Cl_2$ (10 ml), 4-N-tert-butoxycarbonylaminomethylben 1-piperazine (A10, 1.64 g, 4.7 mmol) is added and the mixture is stirred at RT overnight. The reaction solution is diluted with $CH_2Cl_2$ (10 ml) and extracted with a semisaturated aqueous NaCl solution (20 ml). The organic phase is dried over $MgSO_4$, filtered off and concentrated under reduced pressure. Further purification is carried out by chromatography [Tol/Ac (8:2)] over a silica gel column. This gives the title compound (1.8 g) as a colorless solid. TLC, silica gel (glass plates), [toluene/acetone (7:3)], $R_f$=0.40.

MS: calc.: $C_{50}H_{82}N_8O_{10}$ (934.2), found: [$MH^+$] 935.0; [$MNa^+$]957.3

A3. 1,2-Bis[4-trans-4-N-tert-butoxycarbonylaminomethylcyclohexylcarbonyl)-1-piperazinylcarbonyl-1-oxyprop-2-ynyl]benzene A solution of 3-[2-(3-hydroxyprop-1-ynyl)phenyl]prop-2-yn-1-ol (A7, 0.4 g, 2.14 mmol) in absolute $CH_2Cl_2$ (10 ml) is admixed with N,N-carbonyldiimidazole (1.04 g, 6.42 mmol) and stirred at RT for 0.5 h. The reaction solution is diluted with $CH_2Cl_2$ (10 ml) and extracted with a semisaturated aqueous NaCl solution (20 ml). The organic phase is dried over $MgSO_4$, filtered off and concentrated under reduced pressure. The resulting residue is taken up in absolute $CH_2Cl_2$ (10 ml), trans-4-N-tert-butoxycarbonylaminomethylcyclohexylcarbonyl-1-piperazine (A8, 1.53 g, 4.7 mmol) is added and the mixture is stirred at RT overnight. The reaction solution is diluted with $CH_2Cl_2$ (10 ml) and extracted with a semisaturated aqueous NaCl solution (20 ml). The organic phase is dried over $MgSO_4$, filtered off and concentrated under reduced pressure. Further purification is carried out by chromatography [Tol/Ac (8:2)] over a silica gel column. This gives the title compound (1.4 g) as an amorphous solid. TLC, silica gel (glass plates), [toluene/acetone (7:3)], $R_f$=0.40.

MS: calc.: $C_{48}H_{68}N_6O_{10}$ (889.1), found: [$MH^+$] 889.0; [$MNa^+$] 911.3

A4. 1,2-Bis[4-(4-N-tert-butoxycarbonylaminomethylbenzylaminocarbonyl)-1-piperazinyl-carbonyl-1-oxyprop-2-ynyl]benzene A solution of 3-[2-(3-hydroxyprop-1-ynyl)phenyl]prop-2-yn-1-ol (A7, 0.4 g, 2.14 mmol) in absolute $CH_2Cl_2$ (10 ml) is admixed with N,N-carbonyldiimidazole (1.04 g, 6.42 mmol) and stirred at RT for 0.5 h. The reaction solution is diluted with $CH_2Cl_2$ (10 ml) and extracted with a semisaturated aqueous NaCl solution (20 ml). The organic phase is dried over $MgSO_4$, filtered off and concentrated under reduced pressure. The resulting residue is taken up in absolute $CH_2Cl_2$ (10 ml), 4-N-tert-butoxycarbonylaminomethylbenzylaminocarbonyl-1-piperazine (A10, 1.63 g, 4.7 mmol) is added and the mixture is stirred at room temperature overnight. The reaction solution is diluted with $CH_2Cl_2$ (10 ml) and extracted with a semisaturated aqueous NaCl solution (20 ml). The organic phase is dried over $MgSO_4$, filtered off and concentrated under reduced pressure. Further purification is carried out by chromatography [Tol/Ac (6:4)] over a silica gel column. This gives the title compound (1.1 g) as a colorless resin. TLC, silica gel (glass plates), [toluene/acetone (7:3)], $R_f$=0.16.

MS: calc.: $C_{50}H_{62}N_8O_{10}$ (934.2), found: [$MH^+$] 935.0; [$MNa^+$] 957.3

A5. 3-[3-(3-Hydroxyprop-1-ynyl)phenyl]prop-2-yn-1-ol

A solution of 1,3-dibromobenzene (0.6 ml, 5.0 mmol) in n-propylamine (15 ml) is admixed successively with $Pd(Ph_3P)_4$ (116 mg, 2%), CuI (28 mg, 3%) and propargyl alcohol (0.9 ml, 15 mmol) and stirred at RT for 20 h. More $Pd(Ph_3P)_4$ (58 mg, 1%), CuI (14 mg, 1.5%) and propargyl alcohol (0.45 ml, 7.5 mmol) are then added, and the mixture is stirred at reflux for a further 6.5 h. After cooling, the reaction mixture is filtered off with suction over kieselguhr, and the filter cake is washed with ethyl acetate (20 ml). The organic phase is concentrated under reduced pressure. Further purification is carried out by chromatography [Tol/Ac (8:2)] over a silica gel column. This gives the title compound (0.6 g) as a colorless oil. TLC, silica gel (glass plates), [toluene/acetone (8:2)], $R_f$=0.22.

MS: calc.: $C_{12}H_{10}O_2$ (186.2), found: [$M^+$] 186.0

A6. 3-[4-(3-Hydroxyprop-1-ynyl)phenyl]prop-2-yn-1-ol

A solution of 1,4-dibromobenzene (1.18 g, 5.0 mmol) in n-propylamine (15 ml) is admixed successively with $Pd(Ph_3P)_4$ (116 mg, 2%), CuI (28 mg, 3%) and propargyl alcohol (0.9 ml, 15 mmol) and stirred at RT for 1 h and then at reflux for 7 h. More $Pd(Ph_3P)_4$ (58 mg, 1%), CuI (14 mg, 1.5%) and propargyl alcohol (0.45 ml, 7.5 mmol) are then added, and the mixture is stirred at reflux for a further 8 h. After cooling, the reaction mixture is filtered off with suction over kieselguhr and the filter cake is washed with ethyl acetate (20 ml). The organic phase is concentrated under reduced pressure. Further purification is carried out by chromatography [Tol/Ac (8:2)] over a silica gel column. This gives the title compound (0.84 g) as a colorless solid. TLC, silica gel (glass plates), [toluene/acetone (8:2)], $R_f$=0.22.

MS: calc.: $C_{12}H_{10}O_2$ (186.2), found: [$M^+$—H] 185.0; [$M^+$]186.0

A7. 3-[2-(3-Hydroxyprop-1-ynyl)phenyl]prop-2-yn-1-ol

Tetrahedron Letters, 1987, 28 (48), 5981–5984

A8. Trans-4-N-tert-butoxycarbonylamino-methylcyclohexylcarbonyl-1-piperazine

At RT, benzyl 4-{1-[trans-4-(N-tert-butoxycarbonylaminomethyl)cyclohexyl]carbonyl}piperazine-1-carboxylate (A9, 0.4 g, 0.87 mmol) is dissolved in MeOH (20 ml) and admixed with palladium-on-carbon (10% Pd, 0.2 g). Under an atmosphere of hydrogen and at RT, the mixture is stirred in a circulation hydrogenation apparatus for 3 h. After uniform conversion (TLC), the catalyst is filtered off and the solution is concentrated under reduced pressure. This gives the title compound (0.28 g) as a colorless solid. Without any further purification, the compound could be used for the next step. TLC, silica gel, glass plates, [$CH_2Cl_2$/MeOH (9:1)], $R_f$=0.10.

A9. Benzyl 4-(1-[trans-4-N-tert-butoxycarbonylamino-methyl)cyclohexyl]carbonyl}piperazine-1-carboxylate A solution of trans-4-(N-tert-butoxycarbonylaminomethyl)cyclohexanecarboxylic acid (0.40 g, 1.55 mmol) and benzyloxycarbonyl-1-piperazine (0.34 g, 1.55 mmol) in absolute $CH_2Cl_2$ (9 ml) and $Et_3N$ (0.96 ml) is admixed with HOBT (0.16 g, 1.2 mmol) and stirred at RT for 20 min. EDC (0.23 g, 1.2 mmol) is then added, and the mixture is stirred at RT overnight. The reaction solution is diluted with $CH_2Cl_2$ (15 ml) and extracted (2×) with semisaturated aqueous $NH_4Cl$ solution (15 ml), dried over $MgSO_4$, filtered off and concentrated under reduced pressure. Further purification by chromatography [$CH_2Cl_2$/MeOH (9:1)] over a silica gel column gives the title compound (0.71 g) as a colorless powder. TLC, silica gel, glass plates [$CH_2Cl_2$/MeOH (9:1)], $R_f$=0.24.

A10. 1-[4-(tert-Butyloxycarbonylamino-methyl)benzylaminocarbonyl]piperazine 41.7 g (86.4 mmol) of benzyl 4-[4-(tert-butyloxycarbonylaminomethyl)benzylaminocarbonyl]piperazine-1-carboxylate (starting material A11 ) in 1.0 l of methanol are hydrogenated over palladium/carbon (5%) for 4 h. The catalyst is filtered off and the solvent is removed, giving 30.3 g of the title compound as a colorless oil.

A11. Benzyl-4-[4-(tert-butyloxycarbonylamino-methyl)benzylaminocarbonyl]piperazine-1-carboxylate At 0° C., 25.0 g (106 mmol) of 4-(tert-butyloxycarbonylaminomethyl)benzylamine in 150 ml of dichloromethane are added dropwise to a solution of 22.4 g (111 mmol) of 4-nitrophenyl chloroformate in 200 ml of dichloromethane, and the mixture is stirred for 10 min. 15.6 ml (111 mmol) of triethylamine are then added dropwise, and the mixture is stirred at RT for 1.5 h. At 0° C., initially 24.5 g (111 mmol) of benzyl piperazine-1-carboxylate in 80 ml of dichloromethane and then 15.6 ml (111 mmol) of triethylamine are added dropwise. The mixture is stirred at RT for 16 h. The solvent is removed from the reaction mixture and the crude product is chromatographed over silica gel (toluene/ethyl acetate= 1:1). Crystallization from diisopropyl ether gives 41.7 g of the title compound as a colorless solid of m.p. 108–112° C.

A12. 3,4-Bis-(4-N-tert-butoxycarbonylaminomethyl-benzylaminocarbonyl-1-oxyprop-2-ynyl)-thiophene N,N-Carbonyldiimidazol (1.6 g, 9.88 mmol) is added to a solution of 3-[4-(3-hydroxyprop-1-ynyl)thiophene] prop-2-yn-1-ol (A27, 0.4 g, 2.08 mmol) in absolute $CH_2Cl_2$ (15 ml), and the mixture is stirred at RT for 1.5 h. The reaction solution is diluted with $CH_2Cl_2$ (15 ml) and extracted with a semisaturated aqueous NaCl solution (20 ml). The organic phase is dried over $MgSO_4$, filtered off and concentrated under reduced pressure. The resulting residue is taken up in absolute $CH_2Cl_2$ (15 ml), 4-N-tert-butoxycarbonylaminomethylbenzylamine (1.13 g, 4.8 mmol) is added and the mixture is stirred at RT overnight. The resulting precipitate is filtered off with suction, washed with $CH_2Cl_2$ (10 ml) and dried under reduced pressure. This gives the title compound (0.65 g) as a colorless solid. TLC, silica gel (glass plates), [toluene/acetone (7:3)], $R_f$=0.42.

MS: calc.: $C_{38}H_{44}N_4O_8S$ (716.1), found: [$MNH_4^+$] 733.8; [$MNa^+$] 739.0

A13. 3,4-Bis-(3-N-tert-butoxycarbonylaminomethyl-benzylaminocarbonyl-1-oxyprop-2-ynyl)-thiophene N,N-Carbonyldiimidazol (1.6 g, 9.88 mmol) is added to a solution of 3-[4-(3-hydroxyprop-1-ynyl)thiophene] prop-2-yn-1-ol (A27, 0.4 g, 2.08 mmol) in absolute $CH_2Cl_2$ (15 ml), and the mixture is stirred at RT for 1.5 h. The reaction solution is diluted with $CH_2Cl_2$ (15 ml) and extracted with a semisaturated aqueous NaCl solution (20 ml). The organic phase is dried over $MgSO_4$, filtered off and concentrated under reduced pressure. The resulting residue is taken up in absolute $CH_2Cl_2$ (15 ml), 3-N-tert-butoxycarbonylaminomethylbenzylamine (1.13 g, 4.8 mmol) is added and the mixture is stirred at RT overnight. The resulting precipitate is filtered off with suction, washed with $CH_2Cl_2$ (10 ml) and dried under reduced pressure. This gives the title compound (0.62 g) as a colorless solid. TLC, silica gel (glass plates), [toluene/acetone (7:3)], $R_f$=0.31.

MS: calc.: $C_{38}H_{44}N_4O_8S$ (716.1), found: [$MNH_4^+$] 733.8

A14. 1,3-Bis-(4-N-tert-butoxycarbonylaminomethyl-benzylaminocarbonyl-1-oxyprop-2-ynyl)-benzene N,N-Carbonyldiimidazole (1.33 g, 8.21 mmol) is added to a solution of 3-[3-(3-hydroxyprop-1-ynyl)phenyl] prop-2-yn-1-ol (A5, 0.5 g, 2.7 mmol) in absolute $CH_2Cl_2$ (10 ml), and the mixture is stirred at RT for 1 h. The reaction solution is diluted with $CH_2Cl_2$ (15 ml) and extracted with a semi-saturated aqueous NaCl solution. The organic phase is dried over $MgSO_4$, filtered off and concentrated under reduced pressure. The resulting residue is taken up in absolute $CH_2Cl_2$ (10 ml), 4-N-tert-butoxycarbonylaminomethylbenzylamine (1.4 g, 5.9 mmol) is added and the mixture is stirred at RT overnight. The reaction mixture is then admixed with $Et_2O$ (10 ml) and stirred at RT for 0.5 h. The resulting precipitate is filtered off with suction, washed with $CH_2Cl_2$/$Et_2O$/MeOH (1:1:0.5; 10 ml) and dried under reduced pressure. This gives the title compound (1.67 g) as a colorless solid. TLC, silica gel (glass plates) [toluene/acetone (7:3)], $R_f$=0.25.

MS: calc.: $C_{40}H_{46}N_4O_8$ (710.1), found: [$MNa^+$] 733.2

A15. 1,2-Bis-(4-N-tert-butoxycarbonylaminomethyl-benzylaminocarbonyl-1-oxyprop-2-ynyl)-benzene N,N-Carbonyldiimidazole (1.33 g, 8.21 mmol) is added to a solution of 3-[2-(3-hydroxyprop-1-ynyl)phenyl] prop-2-yn-1-ol (A7, 0.5 g, 2.7 mmol) in absolute $CH_2Cl_2$ (10 ml), and the mixture is stirred at RT for 1 h. The reaction solution is diluted with $CH_2Cl_2$ (15 ml) and extracted with a semi-saturated aqueous NaCl solution. The organic phase is dried over $MgSO_4$, filtered off and concentrated under reduced pressure. The resulting residue is taken up in absolute $CH_2Cl_2$ (10 ml), 4-N-tert-butoxycarbonylaminomethylbenzylamine (1.4 g, 5.9 mmol) is added and the mixture is stirred at RT overnight. The reaction mixture is then admixed with $Et_2O$ (10 ml) and stirred at RT for 0.5 h. The resulting precipitate is filtered off with suction, washed with $CH_2Cl_2Et_2O$/MeOH (1:1:0.5; 10 ml) and dried under reduced pressure. This gives the title compound (1.0 g) as a colorless solid. TLC, silica gel (glass plates) [toluene/acetone (7:3)], $R_f$=0.20.

MS: calc.: $C_{40}H_{46}N_4O_8$ (710.1), found: [$MNa^+$] 733.1

A16. 2,5-Bis-(4-N-tert-butoxycarbonylaminomethyl-benzylaminocarbonyl-1-oxyprop-2-ynyl)-furan N,N-Carbonyldiimidazole (1.12 g, 6.91 mmol) is added to a solution of 3-[5-(3-hydroxyprop-1-ynyl)furan] prop-2-yn-1-ol (A28, 0.4 g, 2.27 mmol) in absolute $CH_2Cl_2$ (8 ml), and the mixture is stirred at RT for 1 h. The reaction solution is diluted with $CH_2Cl_2$ (8 ml) and extracted with a semisaturated aqueous NaCl solution (15 ml). The organic phase is dried over $MgSO_4$, filtered off and concentrated under reduced pressure. The resulting residue is taken up in absolute $CH_2Cl_2$ (8 ml), 4-N-tert-butoxycarbonylaminomethylbenzylamine (1.18 g, 5.0 mmol) is added and the mixture is stirred at RT overnight. The reaction mixture is then admixed with $Et_2O$ (8 ml) and stirred at RT for 0.5 h. The resulting precipitate is filtered off with suction, washed with $CH_2Cl_2/Et_2O$/MeOH (1:1:0.5; 8 ml) and dried under reduced pressure. This gives the title compound (1.1 g) as a colorless solid. TLC, silica gel (glass plate), [toluene/acetone (7:3)], $R_f$=0.23.

MS: calc.: $C_{38}H_{44}N_4O_9$ (700.2), found: [$MNH_4^+$] 717.8; [$MNa^+$] 723.1

A17. 2,5-Bis-(3-N-tert-butoxycarbonylaminomethyl-benzylaminocarbonyl-1-oxyprop-2-ynyl)-furan N,N-Carbonyldiimidazole (1.12 g, 6.91 mmol) is added to a solution of 3-[5-(3-hydroxyprop-1-ynyl)furan] prop-2-yn-1-ol (A28, 0.4 g, 2.27 mmol) in absolute $CH_2Cl_2$ (8 ml), and the mixture is stirred at RT for 1 h. The reaction solution is diluted with $CH_2Cl_2$ (8 ml) and extracted with a semisaturated aqueous NaCl solution (15 ml). The organic phase is dried over $MgSO_4$, filtered off and concentrated under reduced pressure. The resulting residue is taken up in absolute $CH_2Cl_2$ (8 ml), 3-N-tert-butoxycarbonylaminomethylbenzylamine (1.18 g, 5.0 mmol) is added and the mixture is stirred at RT overnight. The reaction solution is diluted with $CH_2Cl_2$ (10 ml) and extracted with a semisaturated aqueous NaCl solution (20 ml). The organic phase is dried over $MgSO_4$, filtered off and concentrated under reduced pressure. Further purification is carried out by chromatography [Tol/Ac (8:2)] over a silica gel column. This gives the title compound (0.7 g) as a colorless solid. TLC, silica gel (glass plates), [toluene/acetone (8:2)], $R_f$=0.40.

MS: calc.: $C_{38}H_{44}N_4O_9$ (700.2), found: [$MNH_4^+$] 717.9; [$MH^+$] 700.9

A18. 1,4-Bis-(4-N-tert-butoxycarbonylaminomethyl-benzylaminocarbonylmethyl-1-oxyprop-2-ynyl)benzene HOBT (1.45 g, 10.9 mmol) is added to a solution of {3-[4-(3-carboxymethoxyprop-1-ynyl)phenyl]prop-2-ynyloxy}acetic acid (A32, 0.40 g, 1.3 mmol) and 4-N-tert-butoxycarbonylaminomethylbenzylamine (2.33 g, 9.9 mmol) in absolute $CH_2Cl_2$ (20 ml) and $Et_3N$ (2.5 ml), and the mixture is stirred at RT for 45 min. EDC (2.1 g, 10.9 mmol) is then added, and the mixture is stirred at RT overnight. The reaction solution is diluted with $CH_2Cl_2$ (15 ml) and extracted (2×) with semisaturated aqueous $NH_4Cl$ solution (25 ml), dried over $MgSO_4$, filtered off and concentrated under reduced pressure. Further purification by chromatography [Tol/Ac (8:2)] over a silica gel column gives the title compound (0.75 g) as a colorless powder. TLC, silica gel, glass plates, [Tol/Ac (7:3)], $R_f$=0.5.

MS: calc.: $C_{42}H_{50}N_4O_8$ (738.0), found: [$MH^+$-Boc] 639.1, $MH^+$-2Boc] 539.2

A19. 1,3-Bis-(4-N-tert-butoxycarbonylaminomethyl-benzylaminocarbonylmethyl-1-oxyprop-2-ynyl)benzene HOBT (1.45 g, 10.9 mmol) is added to a solution of {3-[3-(3-carboxymethoxyprop-1-ynyl)phenyl]prop-2-ynyloxy}acetic acid (A30, 0.40 g, 1.3 mmol) and 4-N-tert-butoxycarbonylaminomethylbenzylamine (1.2 g, 5.2 mmol) in absolute $CH_2Cl_2$ (20 ml) and $Et_3N$ (2.5 ml), and the mixture is stirred at RT for 45 min. EDC (2.1 g, 10.9 mmol) is then added, and the mixture is stirred at RT overnight. The reaction solution is diluted with $CH_2Cl_2$ (15 ml) and extracted (2×) with semisaturated aqueous $NH_4Cl$ solution (25 ml), dried over $MgSO_4$, filtered off and concentrated under reduced pressure. Further purification by chromatography [Tol/Ac (8:2)] over a silica gel column gives the title compound (1.1 g) as a colorless powder. TLC, silica gel, glass plates, [Tol/Ac (7:3)], $R_f$=0.51.

MS: calc.: $C_{42}H_{50}N_4O_8$ (738.0), found: [$MH^+$] 738.8, [$MNH_4^+$] 755.8; [$MNa^+$] 761.2

A20. 1,4-Bis-(4-N-tert-butoxycarbonylaminomethyl-benzylcarbonyl-1-aminoprop-2-ynyl)-benzene HOBT (2.17 g, 16.3 mmol) is added to a solution of [4-(tert-butoxycarbonylaminomethyl)phenyl]acetic acid (2.6 g, 9.8 mmol) and 3-[4-(3-aminoprop-1-ynyl)phenyl] prop-2-ynylamine (A23, 0.45 g, 2.44 mmol) in absolute $CH_2Cl_2$ (10 ml) and $Et_3N$ (3.8 ml), and the mixture is stirred at RT for 45 min. EDC (3.1 g, 16.1 mmol) is then added, and the mixture is stirred at RT overnight. The reaction solution is diluted with $CH_2Cl_2$ (15 ml) and extracted (2×) with semisaturated aqueous $NH_4Cl$ solution (25 ml), dried over $MgSO_4$, filtered off and concentrated under reduced pressure. Further purification by chromatography (Tol/Ac (7:3)] over a silica gel column gives the title compound (0.25 g) as a colorless powder. TLC, silica gel, glass plates [Tol/Ac (7:3)], $R_f$=0.49.

MS: calc.: $C_{40}H_{46}N_4O_6$ (678.6), found: [$MNa^+$] 701.1

A21. 1,2-Bis-(4-N-tert-butoxycarbonylaminomethyl-benzylcarbonyl-1-aminoprop-2-ynyl)-benzene HOBT (1.45 g, 7.7 mmol) is added to a solution of [4-(tert-butoxycarbonylaminomethyl)phenyl]acetic acid (1.73 g, 6.52 mmol) and 3-[2-(3-aminoprop-1-ynyl)phenyl] prop-2-ynylamine (A24, 0.3 g, 1.63 mmol) in absolute $CH_2Cl_2$ (7 ml) and $Et_3N$ (2.5 ml), and the mixture is stirred at RT for 45 min. EDC (2.06 g, 7.7 mmol) is then added and the mixture is stirred at RT overnight. The reaction solution is diluted with $CH_2Cl_2$ (7 ml) and extracted (2×) with semisaturated aqueous $NH_4Cl$ solution (25 ml), dried over $MgSO_4$, filtered off and concentrated under reduced pressure. Further purification by chromatography [Tol/Ac (8:2)] over a silica gel column gives the title compound (0.23 g) as a colorless powder. TLC, silica gel, glass plates [Tol/Ac (6:4)], $R_f$=0.36.

MS: calc.: $C_{40}H_{46}N_4O_6$ (678.6), found: [$MH^+$] 678.7, [$MNa^+$] 701.1

A22. 1,4-Bis-(4-N-tert-butoxycarbonylaminomethylphenylethylcarbonyl-1-aminoprop-2-ynyl)-benzene HOBT (1.27 g, 6.7 mmol) is added to a solution of 3-[4-(tert-butoxycarbonylaminomethyl)phenyl] propionic acid (A33, 1.0 g, 3.58 mmol) and 3-[4-(3-aminoprop-1-ynyl) phenyl]prop-2-ynylamine (A23, 0.26 g, 1.41 mmol) in absolute $CH_2Cl_2$ (10 ml) and $Et_3N$ (2.5 ml), and the mixture is stirred at RT for 45 min. EDC (1.82 g, 6.8 mmol) is then added, and the mixture is stirred at RT overnight. The reaction solution is diluted with $CH_2Cl_2$ (7 ml) and extracted (2×) with semisaturated aqueous $NH_4Cl$ solution (25 ml), dried over $MgSO_4$, filtered off and concentrated under reduced pressure. Further purification by chromatography [Tol/Ac (8:2)] over a silica gel column gives the title compound (0.42 g) as a colorless powder. TLC, silica gel, glass plates [Tol/Ac (8:2)], $R_f$=0.48.

MS: calc.: $C_{42}H_{50}N_4O_6$ (706.9), found: [$MNa^+$] 729.0

A23. 3-[4-(3-Aminoprop-1-ynyl)phenyl]prop-2-ynylamine

At RT, hydrazine hydrate (5.1 ml) is added dropwise to a suspension of 1,4-bis-(1-phthalimidoprop-2-ynyl)benzene (A25, 7.8 g, 17.5 mmol) in ethanol (200 ml), and the solution is heated at the boil for 2.5 h. The reaction solution is stirred at RT overnight and then concentrated under reduced pressure. The residue is taken up in $CH_2Cl_2$ (150 ml) and extracted (3×) with aqueous 1 N NaOH solution (150 ml). The combined organic phases are dried over $MgSO_4$, filtered off and concentrated under reduced pressure. This gives the title compound (3 g) as a yellow oil. The compound is used without further purification for the next step.

A24. 3-[2-(3-Aminoprop-1-ynyl)phenyl]prop-2-ynylamine

At RT, hydrazine hydrate (1.1 ml) is added dropwise to a suspension of 1,2-bis-(1-phthalimidoprop-2-ynyl)benzene (A26, 1.5 g, 3.37 mmol) in ethanol (25 ml), and the solution is heated at the boil for 2.5 h. The reaction solution is stirred at RT overnight and then concentrated under reduced pressure. The residue is taken up in $CH_2Cl_2$ (20 ml) and extracted (3×) with aqueous 1 N NaOH solution (20 ml). The combined organic phases are dried over $MgSO_4$, filtered off and concentrated under reduced pressure. This gives the title compound (0.6 g) as a yellow oil. The compound is used without further purification for the next step.

A25. 1,4-Bis-(1-phthalimidoprop-2-ynyl)-benzene

Triphenylphosphine (3.3 g, 12.7 mmol) and phthalimide (1.9 g, 13.5 mmol) are added successively to a solution of 3-[4-(3-hydroxyprop-1-ynyl)phenyl]prop-2-yn-1-ol (A6, 1.2 g, 6.4 mmol) in absolute THF (30 ml). DEAD (2.7 ml, 12.7 mmol) is then added dropwise to the reaction mixture. The mixture is stirred at RT for 2 d and the resulting precipitate is then filtered off and washed with THF (15 ml) and $Et_2O$ (15 ml). The title compound (1.5 g) is obtained as a colorless powder. TLC, silica gel, glass plates, [Tol/Ac (8:2)], $R_f$=0.51.

A26. 1,2-Bis-(1-phthalimidoprop-2-ynyl)-benzene

Triphenylphosphine (1.6 g, 6.3 mmol) and phthalimide (1.0 g, 6.7 mmol) are added successively to a solution of 3-[2-(3-hydroxyprop-1-ynyl)phenyl]prop-2-yn-1-ol (A7, 0.6 g, 3.2 mmol) in absolute THF (20 ml). DEAD (1.35 ml, 6.3 mmol) is then added dropwise to the reaction mixture. The mixture is stirred at RT for 2 d and the resulting precipitate is then filtered off and washed with THF (8 ml) and $Et_2O$ (8 ml). The title compound (0.97 g) is obtained as a colorless powder. TLC, silica gel, glass plates, [Tol/Ac (8:2)], $R_f$=0.60.

A27. 3-[4-(3-Hydroxyprop-1-ynyl)thiophen-3-yl]prop-2-yn-1-ol $Pd(Ph_3P)_4$ (116 mg, 2%), CuI (28 mg, 3%) and propargyl alcohol (0.9 ml, 15 mmol) are added successively to a solution of 3,4-dibromothiophene (1.18 g, 5.0 mmol) in n-propylamine (15 ml), and the reaction mixture is stirred at RT for 1 h and then under reflux for 7 h. More $Pd(Ph_3P)_4$ (58 mg, 1%), CuI (14 mg, 1.5%) and propargyl alcohol (0.45 ml, 7.5 mmol) are then added and the mixture is stirred under reflux for another 8 h. After cooling, the reaction mixture is filtered off through kieselguhr and washed with ethyl acetate (20 ml). The organic phase is concentrated under reduced pressure. Further purification is carried out by chromatography [Tol/Ac (8:2)] over a silica gel column. This gives the title compound (0.84 g) as a colorless solid. TLC, silica gel (glass plates), [toluene/acetone (8:2)], $R_f$=0.22.

MS: calc.: $C_{10}H_8O_2S$ (192.2), found: [$M^+$] 192

A28. 3-[5-(3-Hydroxyprop-1-ynyl)furan-2-yl]prop-2-yn-1-ol $Pd(Ph_3P)_4$ (580 mg, 3%), CuI (140 mg, 2%) and propargyl alcohol (4.65 ml, 67.7 mmol) are added successively to a solution of 2,5-dibromofuran (5.1 g, 22.6 mmol) in n-propylamine (100 ml), and the mixture is stirred at RT for 1 h and then under reflux for 24 h. More propargyl alcohol (2.0 ml, 33 mmol) is then added and the mixture is stirred under reflux for another 8 h. After cooling, the reaction mixture is filtered off with suction through kieselguhr and washed with ethyl acetate (50 ml). The organic phase is concentrated under reduced pressure. Further purification is carried out by chromatography [Tol/Ac (8:2)] over a silica gel column. This gives the title compound (3.8 g) as a colorless solid. TLC, silica gel (glass plates), [toluene/acetone (8:2)], $R_f$=0.40.

MS: calc.: $C_{10}H_8O_3$ (176.2), found: [$M^+$] 176

A29. Methyl {3-[3-(3-carboxymethoxyprop-1-ynyl)phenyl]prop-2-ynyloxy}acetate

A 60% suspension of NaH (2.1 g, 53.7 mmol) is added to a solution of 3-[3-(3-hydroxyprop-1-ynyl)phenyl] prop-2-yn-1-ol (A5, 0.5 g, 2.68 mmol) in absolute THF (20 ml), and the mixture is stirred at 70° C. for 2 h. After cooling to RT, methyl bromoacetate (5.2 ml, 53.7 mmol) is added dropwise to the reaction solution, and the mixture is stirred at RT overnight. For work-up, the reaction solution is poured into an ice-cooled semisaturated aqueous $NH_4Cl$ solution (25 ml) and extracted (2×) with ethyl acetate. The combined organic phases are dried over $MgSO_4$, filtered off and concentrated under reduced pressure. Further purification by chromatography [Tol/Ac (9:1)] over a silica gel column gives the title compound (0.85 g) as a colorless residue. TLC, silica gel, glass plates, [Tol/Ac (7:3)], $R_f$=0.80.

A30. {3-[3-(3-Carboxymethoxyprop-1-ynyl)phenyl] prop-2-ynyloxy} acetic acid

An aqueous 1 N NaOH solution (18 ml) is added dropwise to a solution of methyl {3-[3-(3-carboxymethoxyprop-1-ynyl)phenyl]prop-2-ynyloxy} acetate (A29, 0.85 g, 2.7 mmol) in methanol (50 ml), and the mixture is stirred at RT for 3 h. The pH of the reaction solution is subsequently adjusted to pH 2 using an aqueous 2 N HCl solution. The solution is extracted with ethyl acetate (30 ml, 2×) and washed with a saturated NaCl solution (30 ml). The combined organic phases are dried over $MgSO_4$, filtered off and concentrated under reduced pressure. This gives the title compound (0.43 g) as a colorless powder.

A31. Methyl {3-[4-(3-carboxymethoxyprop-1-ynyl)phenyl]prop-2-ynyloxy}acetate

A 60% suspension of NaH (2.1 g, 53.7 mmol) is added to a solution of 3-[4-(3-hydroxyprop-1-ynyl)-phenyl] prop-2-yn-1-ol (A6, 0.5 g, 2.68 mmol) in absolute THF (20 ml), and the mixture is stirred at 70° C. for 2 h. After cooling to RT, methyl bromoacetate (5.2 ml, 53.7 mmol) is added dropwise to the reaction solution, and the mixture is stirred at RT overnight. For work-up, the reaction solution is poured into an ice-cooled semisaturated aqueous $NH_4Cl$ solution (25 ml) and extracted (2×) with ethyl acetate. The combined organic phases are dried over $MgSO_4$, filtered off and concentrated under reduced pressure. The title compound (0.88 g) is obtained as a colorless powder. TLC, silica gel, glass plates, [Tol/Ac (7:3)], $R_f$=0.70.

A32. {3-[4-(3-Carboxymethoxyprop-1-ynyl)phenyl] prop-2-ynyloxy}acetic acid

An aqueous 2 N NaOH solution (10 ml) is added dropwise to a solution of methyl {3-[4-(3-carboxymethoxyprop-1-ynyl)phenyl]prop-2-ynyloxy)acetate (A31; 0.88 g, 2.7 mmol) in methanol (50 ml), and the mixture is stirred at RT for 2 h. The pH of the reaction solution is then adjusted to pH 2 using an aqueous 2 N HCl solution. The solution is extracted with ethyl acetate (30 ml, 2×) and washed with a saturated NaCl solution (30 ml). The combined organic phases are dried over $MgSO_4$, filtered off and concentrated under reduced pressure. This gives the title compound (0.75 g) as a colorless powder.

A33. 344-tert-Butyloxycarbonylaminomethylphenyl)propionic acid 4.65 g of methyl 3-(4-aminomethylphenyl)propionate hydrochloride (A34) and 6.17 ml of triethylamine are mixed in 20 ml of dichloromethane. To this mixture, a solution of 4.62 g of di-tert-butyl-dicarbonate in 10 ml of dichloromethane is added slowly at 0° C. with stirring. Stirring is continued 1 h at 0° C. and 3 h at RT. Then the reaction mixture is washed twice with 1N hydrochloric acid solution, with sodium hydrogen carbonate solution and water. After drying over magnesium sulfate, the solvent is removed and the residue (5.6 g) is dissolved in 50 ml of tetrahydrofurane. 13.4 ml of 2N aqueous sodium hydroxide solution is added and the mixture is stirred overnight, neutralized with 6.7 ml of 4N hydrochloric acid solution and the organic solvent is distilled off. The white precipitate is filtered by suction, washed with water and dried to give 4.65 g of the title compound.

MS: calc.: $C_{15}H_{21}NO_4$ (279,3), found: [$MNH_4^+$] 297,0

A34. Methyl 3-(4-aminomethylphenyl)propionate hydrochloride 5.6 g of methyl 4-(hydroxyimino-methyl)cinnamate (A35) are dissolved in a mixture of 170 ml of methanol and 50 ml of acetic acid and hydrogenated over 0.5 g palladium/carbon (10%) for four hours. The catalyst is filtered off and the solvents are removed. The residue is stirred with ether and then a solution of hydrogen chloride in ether is added. The white precipitate is filtered by suction, washed with ether and dried in vacuo to give 4.65 g of the title compound.

MS: calc.: $C_{11}H_{15}NO_2$ (193,2), found: [$MH^+$] 194,0

A35. Methyl 4-(hydroxyimino-methyl)cinnamate 4.0 g of methyl 4-formylcinnamate are dissolved in 40 ml methanol and then 1.6 g hydroxylamine-hydrochloride and 1.9 g sodium acetate are added. The mixture is stirred overnight and then diluted with 300 ml water. The precipitate is filtered by suction, dried in vacuo and crystallized from ethyl acetate/petrolether. This gives 3.56 g of the title compound.

MS: calc.: $C_{11}H_{11}NO_3$ (205,2), found: [$MH^+$] 206,0

Commercial Utility

As tryptase inhibitors, the compounds according to the invention have useful pharmacological properties which make them commercially utilizable. Human tryptase is a serin protease which is the main protein in human mast cells. Tryptase comprises eight closely related enzymes (α1, α2, β1a, β1b, β2, β3, mMCP-7-like-1, mMCP-7-like-2; 85 to 99% sequence identity) (cf. Miller et al., J. Clin. Invest. 84 (1989) 1188–1195; Miller et al., J. Clin. Invest. 86 (1990) 864–870; Vanderslice et al., Proc. Natl. Acad. Sci., USA 87 (1990) 3811–3815; Pallaoro et al., J. Biol. Chem. 274 (1999) 3355–3362). However, only the β-tryptases (Schwartz et al., J. Clin. Invest. 96 (1995) 2702–2710; Sakai et al., J. Clin. Invest. 97 (1996) 988–995) are activated intracellularly and stored in catalytically active form in secretory granules. Compared with other known serin proteases, such as, for example, trypsin or chymotrypsin, tryptase has some special properties (Schwartz et al., Methods Enzymol. 244, (1994), 88–100; G. H. Caughey, "Mast cell proteases in immunology and biology". Marcel Dekker, Inc., New York, 1995). Tryptase from human tissue has a noncovalently-linked tetrameric structure which has to be stabilized by heparin or other proteoglycanes to be proteolytically active. Together with other inflammatory mediators, such as, for example, histamine and proteoglycanes, tryptase is released when human mast cells are activated. Because of this, tryptase is thought to play a role in a number of disorders, in particular in allergic and inflammatory disorders, firstly because of the importance of the mast cells in such disorders and secondly since an increased tryptase concentration was observed in a number of disorders of this type. Thus, tryptase is associated, inter alia, with the following diseases: acute and chronic (in particular inflammatory and allergen-induced) airway disorders of various origins (for example bronchitis, allergic bronchitis, bronchial asthma, COPD); interstitial lung disorders; disorders based on allergic reactions of the upper airways, (pharynx, nose) and the adjacent regions (for example paranasal sinuses, conjunctivae), such as, for example allergic conjunctivitis and allergic rhinitis; disorders of the arthritis type (for example rheumatoid arthritis); autoimmune disorders, such as multiple sclerosis; furthermore periodontitis, anaphylaxis, interstitial cystitis, dermatitis, psoriasis, sclerodermia/systemic sclerosis, inflammatory intestinal disorders (Crohn's disease, inflammatory bowel disease) and others. In particular, tryptase seems to be connected directly to the pathogenesis of asthma (Caughey, Am. J. Respir. Cell Mol. Biol. 16 (1997), 621–628; R. Tanaka, "The role of tryptase in allergic inflammation" in: Protease Inhibitors, IBC Library Series, 1979, Chapter 3.3.1–3.3.23).

A further subject of the invention relates to the compounds according to the invention for use in the treatment and/or prophylaxis of diseases, in particular the diseases mentioned.

The invention likewise relates to the use of the compounds according to the invention for preparing medicaments which are employed for the treatment and/or prophylaxis of the diseases mentioned.

Medicaments for the treatment and/or prophylaxis of the diseases mentioned, which contain one or more of the compounds according to the invention, are furthermore a subject of the invention.

The medicaments are prepared by processes which are known per se and familiar to the person skilled in the art. As medicaments, the compounds according to the invention (=active compounds) are either employed as such, or preferably in combination with suitable pharmaceutical excipients, for example in the form of tablets, coated tablets, capsules, suppositories, patches, emulsions, suspension, gels or solutions, the active compound content advantageously being between 0.1 and 95%.

The person skilled in the art is familiar on the basis of his/her expert knowledge with the excipients which are suitable for the desired pharmaceutical formulations. In addition to solvents, gel-forming agents, ointment bases and other active compound vehicles, it is possible to use, for example, antioxidants, dispersants, emulsifiers, preservatives, solubilizers or permeation promoters.

For the treatment of disorders of the respiratory tract, the compounds according to the invention are preferably also administered by inhalation. For this purpose, they are either administered directly as a powder (preferably in micronized form) or by nebulization of solutions or suspensions which contain them. With respect to the preparations and administration forms, reference is made, for example, to the details in European Patent 163 965.

For the treatment of dermatoses, the compounds according to the invention are in particular used in the form of those medicaments which are suitable for topical administration. For the preparation of the medicaments, the compounds according to the invention (=active compounds) are preferably mixed with suitable pharmaceutical excipients and further processed to give suitable pharmaceutical formulations. Suitable pharmaceutical formulations which may be mentioned are, for example, powders, emulsions, suspensions, sprays, oils, ointments, fatty ointments, creams, pastes, gels or solutions.

The medicaments according to the invention are prepared by processes known per se. The dosage of the active compounds in the case of systemic therapy (p.o. or i.v.) is between 0.1 and 10 mg per kilogram per day.

Biological Investigations

The documented pathophysiological effects of mast cell tryptase are caused directly by the enzymatic activity of the protease. Accordingly, they are reduced or blocked by inhibitors which inhibit the enzymatic activity of the tryptase. A suitable measure for the affinity of a reversible inhibitor to the target protease is the equilibrium dissociation constant $K_i$ of the enzyme-inhibitor complex. This $K_i$ value can be determined via the effect of the inhibitor on the tryptase-induced cleavage of a chromogenic peptide-p-nitroanilide substrate or a fluorogenic peptide-aminomethylcoumarin substrate.

Methodology

The dissociation constants for the tryptase-inhibitor complexes are determined under equilibrium conditions in accordance with the general proposals of Bieth (Bieth J G, Pathophysiological Interpretation of kinetic constants of protease inhibitors, Bull. Europ. Physiopath. Resp. 16:183–195, 1980) and the methods of Sommerhoff et al. (Sommerhoff C P et al., A Kazal-type inhibitor of human mast cell tryptase: Isolation from the medical leech Hirudo medicinalis, characterization, and sequence analysis, Biol. Chem. Hoppe-Seyler 375: 685–694, 1994).

Human tryptase is isolated from lung tissue or prepared recombinantly; the specific activity of the protease, determined by titration, is usually greater than 85% of the theoretical value. In the presence of heparin (0.1–50 μg/ml) for stabilizing the protease, constant amounts of the tryptase are incubated with increasing amounts of the inhibitors. After an equilibrium between the reaction partners has formed, the remaining enzyme activity after addition of the peptide-p-nitroanilide substrate tos-Gly-Pro-argpNA is determined and the cleavage of the latter is monitored at 405 nm for 3 min. Alternatively, the remaining enzymatic activity can also be determined using fluorogenic substrates. The apparent dissociation constants $K_{iapp}$ (i.e. in the presence of substrate) are subsequently determined by adapting the enzyme rates to the general equation for reversible inhibitors (Morrison J F, Kinetics of the reversible inhibition of enzyme-catalyzed reactions by tight-binding inhibitors, Biochim. Biophys. Acta 185, 269–286, 1969) using non-linear regression:

$$V_1/V_0=1-\{E_t+I_t+K_{iapp}-[(E_t+I_t+K_{iapp})^2-4E_tI_t]^{1/2}\}/2E_t$$

$V_1$ and $V_0$ are the rates in the presence and absence, respectively, of the inhibitor, and $E_t$ and $I_t$ are the tryptase and inhibitor concentrations, respectively.

The apparent dissociation constants determined for the compounds according to the invention are shown in Table A below, where the numbers of the compounds correspond to the numbers of the compounds in the examples.

TABLE A

Inhibition of human tryptase

| Compound | $K_{iapp}$ ($\mu$M) |
|---|---|
| 1 | 0.003 |
| 2 | 0.01 |
| 3 | 0.2 |
| 4 | 0.003 |
| 5 | 0.032 |
| 6 | 0.3 |
| 7 | 0.12 |
| 8 | 0.08 |
| 9 | 0.0075 |
| 10 | 0.15 |
| 11 | 0.03 |
| 12 | 0.013 |
| 13 | 0.13 |
| 14 | 0.33 |
| 15 | 0.029 |

What is claimed is:

1. A compound of formula I

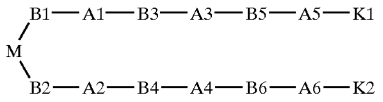

(I)

in which

A1 and A2 are identical or different and are —O—, —C(O)—, —O—C(O)—, —NH—C(O)— or a bond, A3 and A4 are identical or different and are 1,4-piperazinylene or a bond, A5 and A6 are identical or different and are —C(O)—, —C(O)—NH—, —NH—C(O)— or —NH—C(O)—NH—, M is the central building block

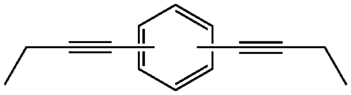

K1 is —B7—(C(O))$_m$—B9—Y1 or —B7—(C(O))$_m$—B9—Z1—B11—X1,

K2 is —B8—(C(O))$_p$—B10—Y2 or —B8—(C(O))$_p$—B10—Z2 —B12—X2,

B1 and B2 are identical or different and are a bond or methylene,

B3, B4, B5 and B6 are identical or different and are a bond or 1–3C-alkylene,

B7, B8, B9 and B10 are identical or different and are a bond or 1–4C-alkylene,

B11 and B12 are identical or different and are a bond or methylene, m is 0, p is 0, X1 and X2 are identical or different and are selected from the groups below

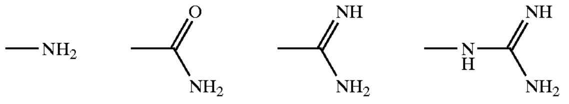

Y1 and Y2 are imidizol-1-yl,

Z1 and Z2 are identical or different and are 5,2-pyridinylene, 6-methyl-5,2-pyridinylene, 4,1-piperidinylene, 3,6-indazolylene, 3,6-indolylene, 1,3-phenylene, 1,4-phenylene, 1,3-cyclohexylene or 1,4-cyclohexylene, and where on the direct route along the bonds between the terminal nitrogen atom as defined in K1 on the one hand and the terminal nitrogen atom as defined in K2 on the other hand, 20 to 40 bonds have to be present, wherein each double bond is counted as one bond and each triple bond is counted as one bond, or a solvate, hydrate, salt, hydrate of a salt or solvate of a salt thereof, or an N-oxide of the nitrogen-containing heteroaryls, heterocycloalkyls, heteroarylenes and heterocycloalkylenes, or a hydrate, salt or hydrate of a salt thereof, wherein the compounds in which one or more of the variables B1, B2, B3, B4, B5, B6, B7, B8, B9, B10, B11 or B12 may assume the meaning of a bond resulting in the direct linkage of two heteroatoms or carbonyl groups are excluded.

2. A compound of formula I according to claim 1, in which

A1 and A2 are —O—C(O)—,

A3 and A4 are 1,4-piperazinylene,

A5 and A6 are identical or different and are —C(O)— or —C(O)—NH—,

M is a central building block selected from the groups below

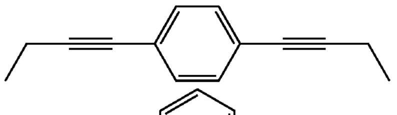

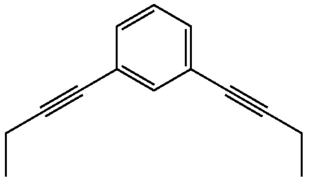

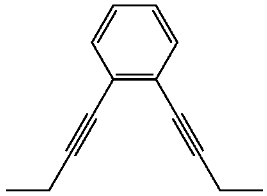

K1 is —B7—(C(O))$_m$—B9—Z1—B11—X1,

K2 is —B8—(C(O))$_p$—B10—Z2—B12—X2,

B1, B2, B3, B4, B5 and B6 are a bond,

B7 and B8 are identical or different and are a bond or methylene,

B9 and B10 are a bond,

B11 and B12 are methylene, m is 0, p is 0,

X1 and X2 are amino,

Z1 and Z2 are identical or different and are 1,4-phenylene or 1,4-cyclohexylene, or a hydrate, salt or hydrate of a salt thereof.

3. A compound of formula I according to claim 1 with the chemical name 1,2-bis[4-trans-4-aminomethylcyclohexylcarbonyl)-1-piperazinylcarbonyl-1-oxyprop-2ynyl]benzene;

1,4-bis[4-trans-4-aminomethylcyclohexylcarbonyl)-1-piperazinylcarbonyl-1-oxyprop-2ynyl]benzene;

1,2-bis[4-(4-aminomethylbenzylaminocarbonyl)-1-piperazinylcarbonyl- 1-oxyprop-2ynyl]benzene;

1,3-bis[4-(4-aminomethylbenzylaminocarbonyl)-1-piperazinylcarbonyl- 1-oxyprop-2ynyl]benzene;

or a hydrate, salt or hydrate of a salt thereof.

4. A pharmaceutical composition comprising a compound of claim 1 or a pharmaceutically acceptable hydrate, salt or hydrate of a salt thereof, or an N-oxide of a compound of claim 1 or a pharmaceutically acceptable hydrate, salt or hydrate of a salt thereof; and a suitable pharmaceutical excipient.

5. A method of treating a disease or disorder in a patient comprising administering to a patient in need thereof a therapeutically effective amount of a compound of claim 1 or a pharmaceutically acceptable hydrate, salt or hydrate of a salt thereof, or an N-oxide of a compound of claim 1 or a pharmaceutically acceptable hydrate, salt or hydrate of a salt thereof, wherein the disease or disorder is selected from the group consisting of asthma, allergic conjunctivitis, allergic rhinitis, psoriasis, sclerodermatitis and inflammatory bowel disease.

6. The method of claim 5, wherein the disease or disorder is asthma.

7. A compound of formula I (I)

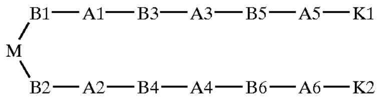

in which

—B1—A1—B3—A3—B5—A5— and —B2—A2—B4—A4—B6—A6— are identical or different and are selected from the groups below

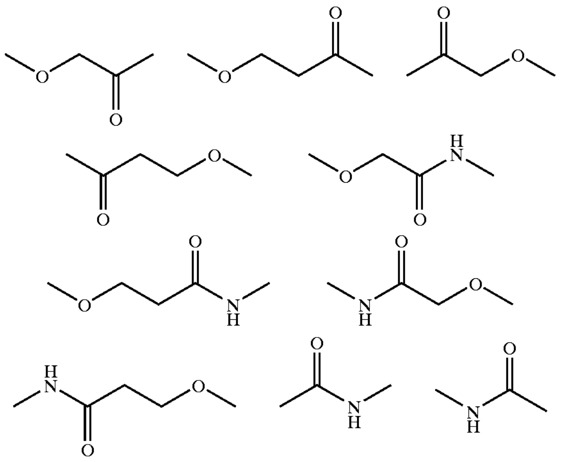

-continued

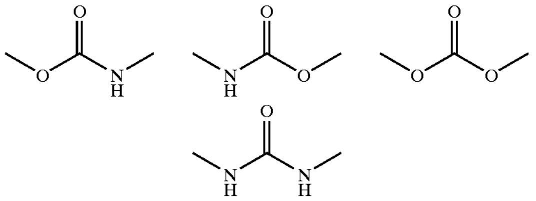

M is the central building block

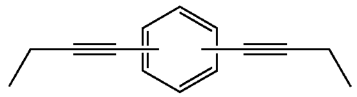

K1 is —B7—$(C(O))_m$—B9—Y1 or —B7—$(C(O))_m$—B9—Z1—B11—X1,

K2 is —B8—$(C(O))_p$—B10—Y2 or —B8—$(C(O))_p$—B10—Z2—B12—X2,

B7, B8, B9, B10, B11 and B12 are identical or different and are a bond or 1–2C-alkylene, m is 0, p is 0, X1 and X2 are identical or different and are selected from the groups below

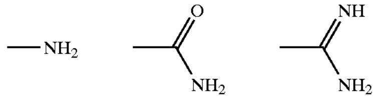

Y1 and Y2 are imidizol-1-yl,

Z1 and Z2 are identical or different and are 5,2-pyridinylene, 6-methyl-5,2-pyridinylene, 4,1-piperidinylene, 3,6-indazolylene, 3,6-indolylene, 1,3-phenylene, 1,4-phenylene, 1,3-cyclohexylene or 1,4-cyclohexylene, and where on the direct route along the bonds between the terminal nitrogen atom as defined in K1 on the one hand and the terminal nitrogen atom as defined in K2 on the other hand, 20 to 40 bonds have to be present, wherein each double bond is counted as one bond and each triple bond is counted as one bond, or a hydrate, salt or hydrate of a salt thereof, or an N-oxide of the nitrogen-containing heteroaryls, heterocycloalkyls, heteroarylenes and heterocycloalkylenes, or a hydrate, salt or hydrate of a salt thereof.

8. A compound of formula I according to claim 7 in which

—B1—A1—B3—A3—B5—A5— and —B2—A2—B4—A4—B6—A6— are identical or different and are selected from

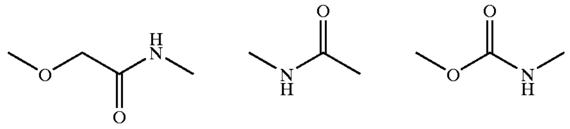

M is the central building block

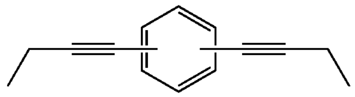

K1 is —B7—(C(O))$_m$—B9—Z1—B11—X1,

K2 is —B8—(C(O))$_p$—B10—Z2—B12—X2,

B7 and B8 are identical or different and are a bond or methylene,

B9 and B10 are a bond,

B11 and B12 are methylene, m is 0, p is 0,

X1 and X2 are amino,

Z1 and Z2 are identical or different and are 1,4-phenylene or 1,3-phenylene, or a hydrate, salt or hydrate of a salt thereof.

9. A compound of formula I according to claim 7 with the chemical name 1,3-Bis-(4-aminomethylbenzylaminocarbonyl-1-oxyprop-2ynyl)-benzene;

1,2-Bis-(4-aminomethylbenzylaminocarbonyl-1-oxyprop-2ynyl)-benzene;

1,4-Bis-(4-aminomethylbenzylaminocarbonylmethyl-1-oxyprop-2-ynyl)-benzene;

1,3-Bis-(4-aminomethylbenzylaminocarbonylmethyl-1-oxyprop-2-ynyl)-benzene;

1,4-Bis-(4-aminomethylbenzylcarbonyl-1-aminoprop-2-ynyl)-benzene;

1,2-Bis-(4-aminomethylbenzylcarbonyl-1-aminoprop-2-ynyl)-benzene;

1,4-Bis-(4-aminomethylphenylethylcarbonyl-1-aminoprop-2ynyl)-benzene;

or a hydrate, salt or hydrate of a salt thereof.

10. A pharmaceutical composition comprising a compound of claim 7 or a pharmaceutically acceptable hydrate, salt or hydrate of a salt thereof, or an N-oxide of a compound of claim 7 or a pharmaceutically acceptable hydrate, salt or hydrate of a salt thereof; and a suitable pharmaceutical excipient.

11. A method of treating a disease or disorder in a patient comprising administering to a patient in need thereof a therapeutically effective amount of a compound of claim 7 or a pharmaceutically acceptable hydrate, salt or hydrate of a salt thereof, or an N-oxide of a compound of claim 7 or a pharmaceutically acceptable hydrate, salt or hydrate of a salt thereof, wherein the disease or disorder is selected from the group consisting of asthma, allergic conjunctivitis, allergic rhinitis psoriasis, sclerodermatitis and inflammatory bowel disease.

12. The method of claim 11, wherein the disease or disorder is asthma.

* * * * *

UNITED STATES PATENT AND TRADEMARK OFFICE

CERTIFICATE OF CORRECTION

PATENT NO. : 6,960,588 B1 
DATED : November 1, 2005
INVENTOR(S) : Martin

It is certified that error appears in the above-identified patent and that said Letters Patent is hereby corrected as shown below:

<u>Column 54,</u>
Line 25, delete “rhinitis psoriasis” and replace with -- rhinitis, psoriasis --.

Signed and Sealed this

Twenty-fourth Day of January, 2006

JON W. DUDAS
*Director of the United States Patent and Trademark Office*